(12) United States Patent
Norén et al.

(10) Patent No.: US 8,886,310 B2
(45) Date of Patent: Nov. 11, 2014

(54) SYSTEM AND METHOD FOR CONTROLLING A HEART STIMULATOR

(75) Inventors: Kjell Norén, Solna (SE); Taraneh G. Farazi, San José, CA (US)

(73) Assignee: St. Jude Medical AB, Jarfalla (SE)

( * ) Notice: Subject to any disclaimer, the term of this patent is extended or adjusted under 35 U.S.C. 154(b) by 1737 days.

(21) Appl. No.: 12/303,987

(22) PCT Filed: Jun. 9, 2006

(86) PCT No.: PCT/SE2006/000699
§ 371 (c)(1),
(2), (4) Date: Oct. 1, 2009

(87) PCT Pub. No.: WO2007/142563
PCT Pub. Date: Dec. 13, 2007

(65) Prior Publication Data
US 2010/0010555 A1    Jan. 14, 2010

(51) Int. Cl.
| *A61N 1/00* | (2006.01) |
| *A61N 1/365* | (2006.01) |
| *A61B 5/024* | (2006.01) |
| *A61N 1/36* | (2006.01) |
| *A61N 1/362* | (2006.01) |
| *A61B 5/00* | (2006.01) |

(52) U.S. Cl.
CPC .............. *A61N 1/365* (2013.01); *A61N 1/3622* (2013.01); *A61B 5/4035* (2013.01); *A61B 5/02405* (2013.01); *A61N 1/36114* (2013.01)
USPC .......................................................... 607/17

(58) Field of Classification Search
USPC .................................... 607/17, 115, 116, 119
See application file for complete search history.

(56) References Cited

U.S. PATENT DOCUMENTS

| 5,203,326 A | 4/1993 | Collins |
| 5,330,507 A | 7/1994 | Schwartz |
| 5,411,025 A | 5/1995 | Webster, Jr. |
| 5,578,061 A | 11/1996 | Stroetmann et al. |
| 5,782,239 A | 7/1998 | Webster, Jr. |
| 5,916,239 A | 6/1999 | Geddes et al. |
| 6,073,048 A | 6/2000 | Kieval et al. |
| 6,319,230 B1 | 11/2001 | Palasis et al. |

(Continued)

OTHER PUBLICATIONS

"Postextrasystolic Regulation Patterns of Blood Pressure and Heart Rate in Patients with Idiopathic Dilated Cardiomyopathy," Voss et al., Journal of Physiology, vol. 538.1 (2002) pp. 271-278.

(Continued)

*Primary Examiner* — Christopher D Koharski
*Assistant Examiner* — Elizabeth K So

(57) ABSTRACT

In a system and method for controlling an implantable stimulator capable of producing pacing pulses to be delivered to cardiac tissue, as well as vagal stimulation pulses to be delivered to vagus nerve sites, upon detection of a premature cardiac event, such as a premature ventricular or atrial contraction, a simulated heart rate turbulence (HRT) procedure is applied if the intrinsic heart rate turbulence is weakened or absent. The simulated HRT includes a first phase in which the heart rate is increased, from the existing level, for a number of heart beats, a second phase in which the heart rate is decreased for a number of heart beats, and an optional third phase in which the heart rate is returned to said existing level.

20 Claims, 13 Drawing Sheets

(56) References Cited

U.S. PATENT DOCUMENTS

| | | |
|---|---|---|
| 6,473,644 B1 | 10/2002 | Terry, Jr. et al. |
| 6,934,583 B2 | 8/2005 | Weinberg et al. |
| 7,142,917 B2 * | 11/2006 | Fukui .............................. 607/14 |
| 7,181,277 B1 | 2/2007 | Shelchuk et al. |
| 7,181,282 B1 * | 2/2007 | Province et al. ................ 607/17 |
| 7,580,747 B1 * | 8/2009 | Farazi et al. .................... 607/25 |
| 2003/0139780 A1 | 7/2003 | Markowitz et al. |
| 2003/0171781 A1 * | 9/2003 | Florio et al. .................... 607/17 |
| 2004/0215289 A1 | 10/2004 | Fukai |

OTHER PUBLICATIONS

"Heart Rate Turbulence: a 5-Year Review," Watanabe et al., Heart Rhythm, vol. 1 (2004) pp. 732-738.

"Mechanism Involved in Heart Rate Turbulence," Wichterle et al., Cardio Electrophysiology Review, vol. 6 (2002) pp. 262-266.

"Heart Rate Turbulence: A new Predictor for Risk of Sudden Cardiac Death," Francis et al., Ann. Non-Invasive Electrocardiology, vol. 10, No. 1 (2005), pp. 102-109.

"Role of Hypotension in Heart Rate Turbulence Physiology," Raj et al., Heart Rhythm, vol. 2, (2005) pp. 820-827.

\* cited by examiner

SYSTEM AND METHOD FOR CONTROLLING A HEART STIMULATOR

FIELD OF THE INVENTION

The present invention generally relates to the field of implantable heart stimulation devices, such as pacemakers, implantable cardioverter-defibrillators (ICD), and similar cardiac stimulation devices. More specifically, the present invention relates to a system for controlling an implantable heart stimulator, an implantable heart stimulator including such a system, a method for operating an implantable heart stimulator, a computer program product and a computer readable medium.

DESCRIPTION OF THE PRIOR ART

Heart Rate Turbulence (HRT) is a dual-phased physiological response of the sinus node to a premature ventricular event or contraction (PVC), for instance a ventricular extra systole (VES), which in turn is an intrinsic ventricular contraction occurring early in relation to when the next regular ventricular contraction is expected. The first or initial phase of the HRT consists of a short acceleration of the heart rate, and the second or subsequent phase consists of a deceleration of the heart rate. In other words, following a PVC in a healthy heart and ensuing compensatory pause, the RR interval is first shortened and the heart rate thereby increased in relation to the heart rate immediately prior to the PVC. Then, the RR interval is extended and the heart rate thereby decreased for a number of heart beats until the heart rate eventually is returned to its initial frequency.

The premature ventricular contraction causes a brief disturbance of the arterial blood pressure. When the autonomic control system is intact, i.e. in a healthy subject, this rapid change is immediately registered with an instantaneous response in the form of heart rate turbulence, HRT. However, if the autonomic control system is impaired, the reaction of HRT may be either weakened or absent.

Studies have shown that patients where HRT is absent or weakened suffer a higher risk of sudden cardiac death. Furthermore, for low risk patients with ischemic heart disease, HRT is a consistent phenomenon. Thus, according to studies, the weakening and absence of HRT can be used as a powerful indicator for identifying patients with cardiac diseases. Reference is made to "Heart rate turbulence: a new predictor for risk of sudden cardiac death", J. Francis et al., Ann Noninvasive Electrocardiol. 2005, 10(1):102-9; "Postextrasystolic regulation patterns of blood pressure and heart rate in patients with idiopathic dilated cardiomyopathy", Andreas Voss et al., Journal of Physiology (2002), 538.1, pp. 271-278; and "Mechanisms Involved in Heart Rate turbulence", Dan Wichterle et al., Cardiac Electrophysiology Review 2002, 6:262-266.

Thus, it is known in the art to use the occurrence and strength of the heart rate turbulence response to premature ventricular or atrial contractions, intrinsic or pacing induced, of a patient for diagnostic purposes, e.g. to detect the presence of cardiac ischemia, or evaluate the risk of sudden cardiac death.

SUMMARY OF THE INVENTION

An object of the present invention is to provide a device and method for reducing the risk of sudden cardiac death.

According to one aspect of the present invention, there is provided a system for controlling an implantable heart stimulator arranged for delivering stimulation pulses to a human heart. The system is connectable to at least one lead comprising an electrode for picking up electrical cardiac signals, to at least one lead comprising one or more electrodes for delivering stimulation pulses to cardiac tissue in at least one ventricle of a heart, and to at least one lead comprising one or more electrodes for delivering vagal stimulation pulses to a vagus nerve site. The system has a signal processing circuit adapted for receiving electrical signals indicative of cardiac contractions, for determining whether a premature cardiac contraction has occurred, and for indicating the occurrence of a premature cardiac contraction. The system further has a controller adapted for initiating and controlling a heart rate turbulence procedure upon the occurrence of a premature cardiac contraction, in which the heart stimulator is controlled to first accelerate the heart rate to an accelerated rate above an existing heart rate at the occurrence of said premature contraction, and then to decelerate the heart rate to a decelerated rate below said existing heart rate.

According to another aspect of the present invention, there is provided an implantable heart stimulator for delivering stimulation pulses to a human heart. The heart stimulator is connectable to at least one lead comprising an electrode for picking up electrical cardiac signals, to at least one lead comprising one or more electrodes for delivering stimulation pacing pulses to cardiac tissue in at least one ventricle of a heart, and to at least one lead carrying one or more electrodes for delivering vagal stimulation pulses to a vagus nerve site. Furthermore, the heart stimulator has a first pulse generator for producing said pacing pulses to cardiac tissue, a second pulse generator for producing said vagal stimulation pulses, and a system as described in the preceding paragraph.

According to a further aspect of the present invention, there is provided a method for operating an implantable heart stimulator, wherein the heart stimulator is connectable to at least one lead carrying electrodes for delivering stimulating pacing pulses to cardiac tissue, and to at least one lead comprising electrodes for delivering vagal stimulation pulses to a vagus nerve site, and wherein the heart stimulator has a first pulse generator adapted to produce said pacing pulses, a second pulse generator for producing the vagal stimulation pulses, and control circuitry for controlling the delivery of the pacing and vagal stimulation pulses. The method includes the steps of determining whether a premature cardiac contraction has occurred, and initiating a heart rate turbulence procedure. The heart rate turbulence procedure includes accelerating the heart rate to an accelerated rate above the existing heart rate at the occurrence of said premature contraction, and then decelerating the heart rate to a decelerated rate below said existing heart rate.

According to still further aspects of the invention, there is provided a computer program product for performing the steps of the method described above, and a computer readable medium encoded with programming instructions for causing a computer to perform the steps of the method described above.

Thus, the invention relates to a heart rate therapy procedure induced by an implantable heart stimulator for simulating the heart rate turbulence (HRT) occurring in a healthy heart. The purpose is to increase cardiac output and coronary flow, and reduce the occurrence of ischemia in the cardiac tissue, which could result in sudden cardiac death, following a premature event, such as a PVC or a VES.

The invention is intended for patients where HRT following a premature cardiac event is absent or in other ways diminished. For example, the intrinsic HRT response could present an insufficient heart rate increase, i.e. the heart rate does not increase to the same extent as in a healthy heart during HRT, the onset of HRT is delayed, the extent of heart rate decrease is reduced, etc.

According to exemplifying embodiments, an implantable cardiac stimulator capable of delivering pacing pulses to cardiac tissue and vagal stimulation pulses to a vagus nerve site is utilized. Upon detection of a premature cardiac contraction, a simulated HRT procedure is initiated. The procedure comprises a first phase in which the heart rate is accelerated or increased for a first successive number of heart beats, and a second phase in which the heart rate is decreased or decelerated for a second successive number of heart beats.

The invention is applicable for patients where it has been established that intrinsic HRT response is weakened or absent, as well as for patients suspected to experience weakened or absent HRT. The latter includes diabetes patients and post MI patients.

According to exemplifying embodiments, the presence and degree of intrinsic HRT is monitored. If weakened or absent HRT has been determined, the simulated HRT procedure is activated. The monitoring of intrinsic HRT may be performed by detecting premature cardiac contractions, and measuring the intrinsic response, e.g. the RR intervals for a number of heart beats, following such a premature contraction. Alternatively, a pacing pulse may be prematurely delivered to induce an HRT response, and a corresponding measurement of the intrinsic response may then follow. Such a determination of the degree of HRT may use the result from at least one premature event, intrinsic or pacer induced. Preferably, the results of a number, e.g. 5, of premature events are used for determining the degree of HRT of a patient's heart.

Generally, a premature cardiac contraction is detected by detecting electrical signals representing the contraction, i.e. depolarization signals of the cardiac tissue. For instance, if the electrode(s) for picking up electrical cardiac signals has detected two subsequent R-waves, without the occurrence of a P-wave in between the R-waves, then the second R-wave represents a premature ventricular contraction (PVC) or ventricular extra systole (VES).

Furthermore, it should be noted that the term vagus nerve site is intended to encompass stimulation to the vagus nerve itself, as well as any nerve or organ that would directly result in a vagal nerve signal effecting a heart rate reduction, such as the baroreceptors. In other words, a stimulation pulse applied to the baroreceptors resulting in a stimulation of the vagus nerve is intended to be encompassed in the expression "vagal stimulation". Stimulation of a vagus nerve or baroreceptors for the purpose of, inter alia, reducing heart rate is known. Examples can be found in U.S. Pat. No. 5,578,061 to Stroetmann et al.; U.S. Pat. No. 6,073,048 to Kieval et al.; and in European Patent Publication No. EP 1 304 135 A2, which are all incorporated herein by reference.

It should be noted that the invention is not restricted to a particular vagus nerve site at which the vagal stimulation pulse is applied. However, for exemplifying purposes only, the vagal stimulation pulses may for example be applied directly to the right or left cervical vagal trunk, transvenously to the right or left cardiac branches of the vagus nerves or to epicedial fatpads, or epicardially to the fatpads. Examples of stimulating particular vagus nerve sites will be described in more detail below.

The heart rate increase during the first phase is performed by delivering stimulation or pacing pulses having an increased frequency in relation to the existing or pre-existing, heart rate at the onset of the simulated HRT therapy, i.e. at the occurrence of the premature contraction. The heart rate increase during the first phase is preferably, but not restricted to, a gradual one. In other words, the interval between successive pacing pulses is gradually decreased for a number of heart beats. This is similar to the behavior during a naturally occurring HRT in a healthy heart. However, an increased heart rate that is maintained at essentially the same frequency during said first phase of the simulated HRT is also contemplated.

In exemplifying embodiments, the increased heart rate during the first phase is performed for 2-4 heart beats. Furthermore, the gradual increase in heart rate during the first phase is in exemplifying embodiments 2-4 percent for each successive beat.

The heart rate decrease in the second phase is performed by delivering vagal stimulation pulses to a vagus nerve site. The voltage, duration and energy contents of the vagal stimulation pulses are adapted for each patient in order to arrive at a suitable deceleration or slowing of the heart rate. A description on how the parameters of the vagal stimulation pulses may be determined will be provided below in more detail below. During the second phase, the heart rate is decreased, through vagal stimulation, from the increased heart rate obtained during the first phase, to a decreased heart rate having a frequency that is lower than the pre-existing heart rate frequency at the occurrence of the premature contraction.

In exemplifying embodiments, the decreased heart rate during the second phase is performed for about 4 15 heart beats, preferably about 7-10 heart beats, adapted to the needs of the patient. Furthermore, the decrease in heart rate during the second phase is preferably gradual, at least until the heart rate reaches a desired lowest level. Then, the gradual decrease in heart rate during the second phase is according to exemplifying embodiments 1-5 percent for each successive beat, preferably about 2 4 percent.

Furthermore, according to further exemplifying embodiments, a third phase is optionally provided. During this third phase, the heart rate is returned, i.e. increased, to essentially the heart rate existing at the occurrence of the premature contraction. This heart rate increase at the end of the simulated HRT procedure may be performed by delivering pacing pulses at a gradually increased rate. Alternatively, the delivery of vagal stimulation pulses is ceased and the patent's intrinsic heart rate returns to the pre-existing heart rate without the aid of pacing pulses. In the alternative embodiment, the heart rate is suitably monitored and pacing pulses are applied to increase the heart rate if the desired rise in intrinsic heart rate is absent or too slow.

According to further embodiments, the duration of each phase, i.e. the number of beats during which there is a heart rate increase and decrease, respectively, could be programmable and/or optimized by the device for improving patient performance. Furthermore, the amount of rate increase and decrease, respectively, by each successive pulse in the first, the second, and the optional third phase could also be programmable values, and/or be optimized by the device for improving performance.

It should be noted that the vagal stimulation pulses may be delivered not only during the second phase of the simulated HRT procedure, but also during the first and optional third phase. Then, the resulting effect of a decreased heart rate is compensated for and overridden by the delivery of pacing pulses at a selected heart rate.

In a first example, the parameters of the vagal stimulation are selected to result in the desired lowest heart rate, i.e. longest RR interval, intended to be achieved during the HRT procedure. Alternatively, the parameters are set to result in a lower heart rate, i.e. an RR interval that is longer, than what is intended during the entire HRT procedure. Then, the heart rate is intended to be controlled by the delivery of pacing pulses essentially throughout the HRT procedure. A benefit of using such an HRT algorithm is that it is very easy to implement, since the setting of the vagal stimulation pulses would only have to ensure that a resulting heart rate would be less than or equal to lowest heart rate that is intended during the HRT procedure. However, the vagal stimulation pulses and the pacing pulses would be delivered simultaneously, which could result in an increased energy consumption.

In a second example, the vagal stimulation pulses are only applied during the second phase of the simulated HRT procedure, i.e. during the decelerated heart rate phase. Then, notwithstanding back-up pacing, the pacing pulses would only have to be delivered during the first phase and as possible back-up pulses during an optional third phase. This would possibly reduce energy consumption, but result in higher demands in terms of the parameters for vagal stimulation pulse delivery. One reason is that the vagal stimulation pulses would in terms of voltage and/or energy content have to be continuously changed to correspond to the desired change in heart rate. Furthermore, the resulting heart rate may need to be continuously monitored in order to determine possible changes in effect of the vagal stimulation pulses over time.

According to exemplifying embodiments, the measurements, applied pacing and vagal stimulation parameters and resulting heart rate responses of each therapy episode are stored for future retrieval at follow-up visits to a physician. Furthermore, the stimulation algorithm is preferably adapted on the basis of the heart rate responses of previous therapy episodes.

It should be noted that the premature cardiac contraction may be a premature ventricular contraction (PVC or VES) or a premature atrial contraction (PAC). It should also be noted that the HRT algorithms may be different for PVC triggered HRT procedure than for PAC triggered HRT procedures.

Furthermore, the embodiments of this application are not restricted to an intrinsic PVC or PAC. On the contrary, simulated HRT procedures triggered by premature contractions in response to pacing stimuli are also contemplated and within the scope of this application.

Further objects and advantages of the present invention will be discussed below by means of exemplifying embodiments.

DESCRIPTION OF THE PREFERRED EMBODIMENTS

The following is a description of exemplifying embodiments. This description is not to be taken in a limiting sense, but is made merely for the purpose of describing general principles of the invention. Thus, even though particular types of heart stimulators will be described, the invention is also applicable to any other types of cardiac stimulators having pacing and vagal stimulation capabilities.

Figure 1:
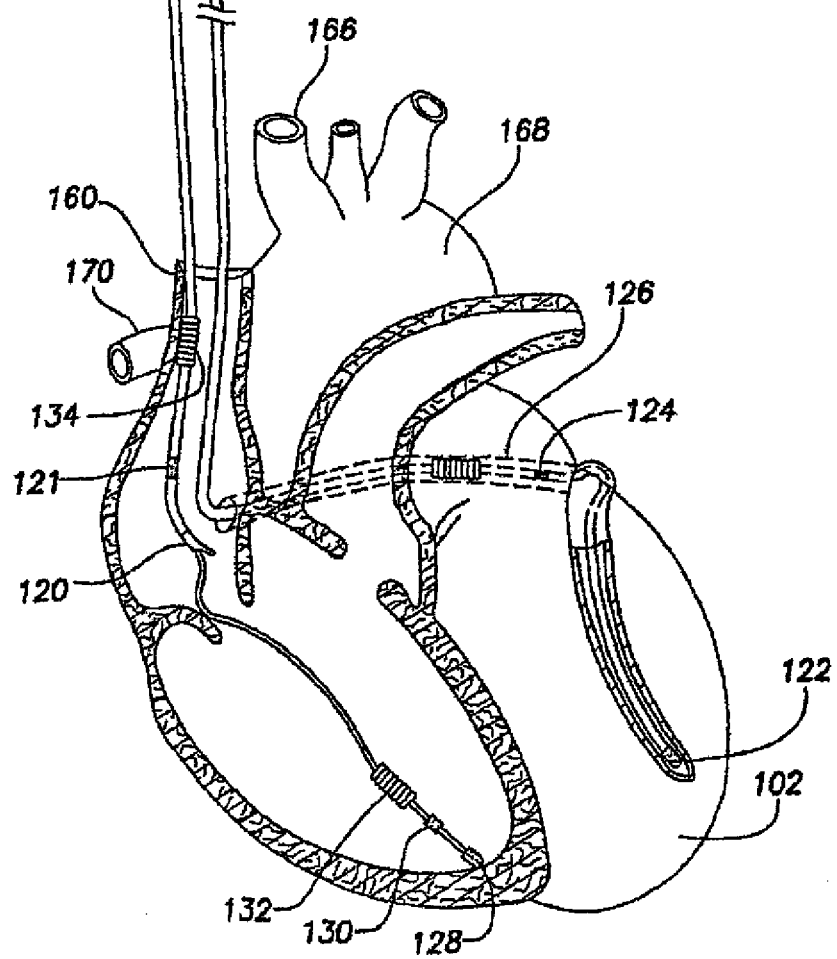
FIG. 1 illustrates two prior art single-pass leads capable of delivering multi-chamber stimulation and shock therapy.

With reference first to FIG. 1, there will now be described an exemplary prior art stimulation device 100 for which the following exemplifying embodiments are applicable. The stimulation device 100 is in electrical communication with a patient's heart 102 by way of three electrical "connections" 104, 106, and 108, suitable for delivering multi-chamber stimulation and shock therapy. While two of the electrical connections (104 and 108) are shown as a single-pass lead, it is to be understood that individual leads could also be used to describe the fundamentals of multi-chamber stimulation. Accordingly, the term electrical "connections" will be used herein to describe the system that makes contact with an electrode, whether it is by a single-pass lead or an individual lead.

To sense atrial cardiac signals and to provide right atrial chamber stimulation therapy, stimulation device 100 is coupled to an implantable right atrial electrical connection 104, coupled to at least an atrial tip electrode 120 and optionally an atrial ring electrode 121, which typically is implanted in the patient's right atrial appendage.

Stimulation device 100 is also shown in electrical communication with the patient's heart 102 by way of an implantable right ventricular connection 108 having, in this implementation, a right ventricular tip electrode 128, a right ventricular ring electrode 130, a right ventricular (RV) coil electrode 132, and an SVC coil electrode 134. Accordingly, the right ventricular connection 108 is capable of sensing or receiving cardiac signals, and delivering stimulation in the form of pacing and shock therapy to the right ventricle.

To sense left atrial and ventricular cardiac signals and to provide left chamber pacing therapy, stimulation device 100 is coupled to a single-pass coronary sinus connection 106, that is, a lead designed for placement in the coronary sinus region via the coronary sinus for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, an exemplary coronary sinus connection 106 is designed to receive atrial and ventricular cardiac signals and to deliver left ventricular pacing therapy using at least a left ventricular tip electrode 122, left atrial pacing therapy using at least a left atrial ring electrode 124, and shocking therapy using, for example a left atrial coil electrode 126 (or a left ventricular coil electrode, not shown, or both). For a complete description of a coronary sinus lead, the reader is directed to U.S. patent application Ser. No. 09/457,277, entitled "A Self-Anchoring, Steerable Coronary Sinus Lead" (Pianca et. al).

Figure 2:
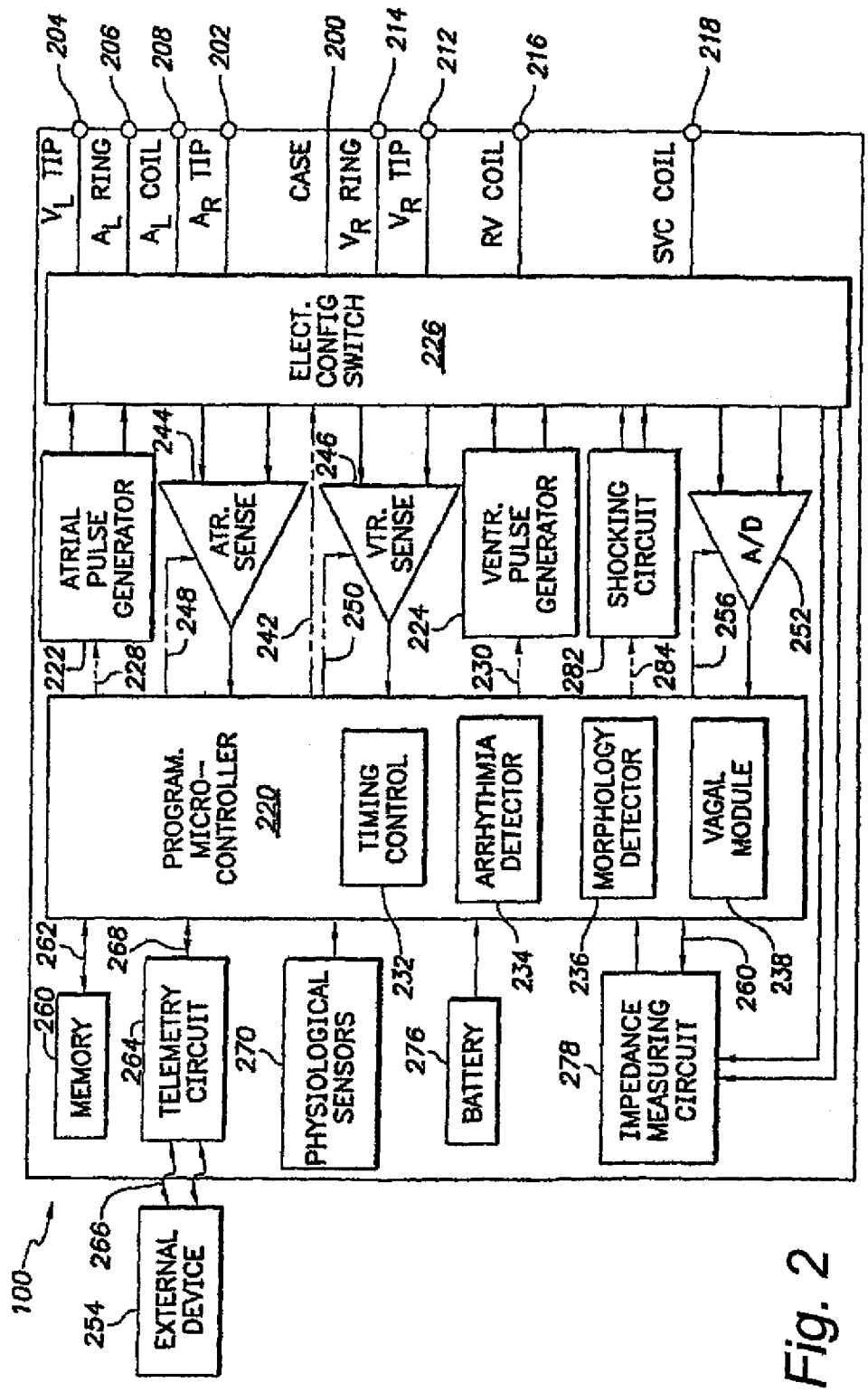
FIG. 2 is a functional block diagram of a multi-chamber implantable stimulation device illustrating basic elements that are configured to provide cardioversion, defibrillation, bradycardia pacing stimulation in four chambers of the heart, in addition to vagal stimulation.

FIG. 2 shows an exemplary, simplified block diagram depicting various components of stimulation device 100. The stimulation device 100 can be capable of treating both fast and slow arrhythmias with stimulation therapy, including cardioversion, defibrillation, and pacing stimulation. While a particular multi-chamber device is shown, it is to be appreciated and understood that this is done for illustration purposes only. Thus, the techniques and methods described below can be implemented in connection with any suitably configured or configurable stimulation device. Accordingly, one of skill in the art could readily duplicate, eliminate, or disable the appropriate circuitry in any desired combination to provide a device capable of treating the appropriate chamber(s) with cardioversion, defibrillation, and pacing stimulation.

Housing 200 for stimulation device 100 is often referred to as the "can", "case" or "case electrode", and may be programmably selected to act as the return electrode for all "unipolar" modes. Housing 200 may further be used as a return electrode alone or in combination with one or more of the coil electrodes 126, 132 and 134 for shocking purposes. Housing 200 further includes a connector (not shown) having a plurality of terminals 202, 204, 206, 208, 212, 214, 216, and 218 (shown schematically and, for convenience, the names of the electrodes to which they are connected are shown next to the terminals).

To achieve right atrial sensing and pacing, the connector includes at least a right atrial tip terminal (AR TIP) 202 adapted for connection to the atrial tip electrode 120. To achieve left chamber sensing, pacing, and shocking, the connector includes at least a left ventricular tip terminal (VL TIP) 204, a left atrial ring terminal (AL RING) 206, and a left atrial shocking terminal (AL COIL) 208, which are adapted for connection to the left ventricular tip electrode 122, the left atrial ring electrode 124, and the left atrial coil electrode 126, respectively.

To support right chamber sensing, pacing, and shocking, the connector further includes a right ventricular tip terminal (VR TIP) 212, a right ventricular ring terminal (VR RING) 214, a right ventricular shocking terminal (RV COIL) 216, and a superior vena cava shocking terminal (SVC COIL) 218, which are adapted for connection to the right ventricular tip electrode 128, right ventricular ring electrode 130, the RV coil electrode 132, and the SVC coil electrode 134, respectively.

At the core of the stimulation device 100 is a programmable microcontroller 220 that controls the various modes of stimulation therapy. As is well known in the art, microcontroller 220 typically includes a microprocessor, or equivalent control circuitry, designed specifically for controlling the delivery of stimulation therapy, and may further include RAM or ROM memory, logic and timing circuitry, state machine circuitry, and I/O circuitry. Typically, microcontroller 220 includes the ability to process or monitor input signals (data or information) as controlled by a program code stored in a designated block of memory. The type of microcontroller is not critical to the described implementations. Rather, any suitable microcontroller 220 may be used that carries out the functions described herein. The use of microprocessor-based control circuits for performing timing and data analysis functions are well known in the art.

FIG. 2 also shows an atrial pulse generator 222 and a ventricular pulse generator 224 that generate pacing stimulation pulses for delivery by the right atrial connection 104, the coronary sinus connection 106, and/or the right ventricular connection 108 via an electrode configuration switch 226. It is understood that in order to provide stimulation therapy in each of the four chambers of the heart, the atrial and ventricular pulse generators, 222 and 224, may include dedicated, independent pulse generators, multiplexed pulse generators, or shared pulse generators. The pulse generators 222 and 224 are controlled by the microcontroller 220 via appropriate control signals 228 and 230, respectively, to trigger or inhibit the stimulation pulses.

Microcontroller 220 further includes timing control circuitry 232 to control the timing of the stimulation pulses (e.g., pacing rate, atrioventricular (AV) delay, atrial interconduction (A-A) delay, or ventricular interconduction (V-V) delay, etc.) as well as to keep track of the timing of refractory periods, blanking intervals, noise detection windows, evoked response windows, alert intervals, marker channel timing, etc., which is well known in the art.

Microcontroller 220 further includes an arrhythmia detector 234, a morphology detector 236, and optionally an orthostatic compensator and a minute ventilation (MV) response module, the latter two are not shown in FIG. 2. These components can be utilized by the stimulation device 100 for determining desirable times to administer various therapies, including those to reduce the effects of orthostatic hypotension. The aforementioned components may be implemented in hardware as part of the microcontroller 220, or as software/firmware instructions programmed into the device and executed on the microcontroller 220 during certain modes of operation.

Microcontroller 220 further includes a vagal module 238 for performing a variety of tasks related to vagal stimulation. This component can be utilized by the stimulation device 100 for determining desirable times to administer various therapies, including timing, frequency of pulse trains, amplitude and pulse duration for vagal stimulation in order to control heart rate. The vagal module 238 may be implemented in hardware as part of the microcontroller 220, or as software/firmware instructions programmed into the device and executed on the microcontroller 220 during certain modes of operation.

The electronic configuration switch 226 includes a plurality of switches for connecting the desired electrodes to the appropriate I/O circuits, thereby providing complete electrode programmability. Accordingly, switch 226, in response to a control signal 242 from the microcontroller 220, determines the polarity of the stimulation pulses (e.g., unipolar, bipolar, combipolar, etc.) by selectively closing the appropriate combination of switches (not shown) as is known in the art.

Atrial sensing circuits 244 and ventricular sensing circuits 246 may also be selectively coupled to the right atrial connection 104, coronary sinus connection 106, and the right ventricular connection 108, through the switch 226 for detecting the presence of cardiac activity in each of the four chambers of the heart. Accordingly, the atrial (ATR. SENSE) and ventricular (VTR. SENSE) sensing circuits, 244 and 246, may include dedicated sense amplifiers, multiplexed amplifiers, or shared amplifiers. Switch 226 determines the "sensing polarity" of the cardiac signal by selectively closing the appropriate switches, as is also known in the art. In this way, the clinician may program the sensing polarity independent of the stimulation polarity. The sensing circuits (e.g., 244 and 246) are optionally capable of obtaining information indicative of tissue capture.

Each sensing circuit 244 and 246 preferably employs one or more low power, precision amplifiers with programmable gain and/or automatic gain control, bandpass filtering, and a threshold detection circuit, as known in the art, to selectively sense the cardiac signal of interest. The automatic gain control enables the device 100 to deal effectively with the difficult problem of sensing the low amplitude signal characteristics of atrial or ventricular fibrillation.

The outputs of the atrial and ventricular sensing circuits 244 and 246 are connected to the microcontroller 220, which, in turn, is able to trigger or inhibit the atrial and ventricular pulse generators 222 and 224, respectively, in a demand fashion in response to the absence or presence of cardiac activity in the appropriate chambers of the heart.

Furthermore, as described herein, the microcontroller 220 is also capable of analyzing information output from the sensing circuits 244 and 246 and/or the data acquisition system 252 to determine or detect whether and to what degree tissue capture has occurred and to program a pulse, or pulses, in response to such determinations. The sensing circuits 244 and 246, in turn, receive control signals over signal lines 248 and 250 from the microcontroller 220 for purposes of controlling the gain, threshold, polarization charge removal circuitry (not shown), and the timing of any blocking circuitry (not shown) coupled to the inputs of the sensing circuits, 244 and 246, as is known in the art.

For arrhythmia detection, the device 100 utilizes the atrial and ventricular sensing circuits, 244 and 246, to sense cardiac signals to determine whether a rhythm is physiologic or pathologic. In reference to arrhythmias, as used herein, "sensing" is reserved for the noting of an electrical signal or obtaining data (information), and "detection" is the processing (analysis) of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the arrhythmia detector 234 of the microcontroller 220 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

Cardiac signals are also applied to inputs of an analog-to-digital (A/D) data acquisition system 252. The data acquisition system 252 is configured to acquire intracardiac electrogram signals, convert the raw analog data into a digital signal, and store the digital signals for later processing and/or telemetric transmission to an external device 254. The data acquisition system 252 is coupled to the right atrial connection 104, the coronary sinus connection 106, and the right ventricular connection 108 through the switch 226 to sample cardiac signals across any pair of desired electrodes.

The microcontroller 220 is further coupled to a memory 260 by a suitable data/address bus 262, wherein the programmable operating parameters used by the microcontroller 220 are stored and modified, as required, in order to customize the operation of the stimulation device 100 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 102 within each respective tier of therapy. One feature of the described embodiments is the ability to sense and store a relatively large amount of data (e.g., from the data acquisition system 252), which data may then be used for subsequent analysis to guide the programming of the device.

Advantageously, the operating parameters of the implantable device 100 may be non-invasively programmed into the memory 260 through a telemetry circuit 264 in telemetric communication via communication link 266 with the external device 254, such as a programmer, transtelephonic transceiver, or a diagnostic system analyzer. The microcontroller 220 activates the telemetry circuit 264 with a control signal 268. The telemetry circuit 264 advantageously allows intracardiac electrograms and status information relating to the operation of the device 100 (as contained in the microcontroller 220 or memory 260) to be sent to the external device 254 through an established communication link 266.

The stimulation device 100 can further include a physiologic sensor 270, commonly referred to as a "rate-responsive" sensor because it is typically used to adjust pacing stimulation rate according to the exercise state of the patient. However, the physiological sensor 270 may further be used to detect changes in cardiac output, changes in the physiological condition of the heart, or diurnal changes in activity (e.g., detecting sleep and wake states). Accordingly, the microcontroller 220 responds by adjusting the various pacing parameters (such as rate, AV Delay, V-V Delay, etc.) at which the atrial and ventricular pulse generators, 222 and 224, generate stimulation pulses. Physiologic sensors may be optionally utilized to confirm hemodynamic improvement following vagal stimulation.

While shown as being included within the stimulation device 100, it is to be understood that the physiologic sensor 270 may also be external to the stimulation device 100, yet still be implanted within or carried by the patient. Examples of physiologic sensors that may be implemented in device 100 include known sensors that, for example, sense respiration rate, pH of blood, ventricular gradient, and so forth. Another sensor that may be used is one that detects activity variance, wherein an activity sensor is monitored diurnally to detect the low variance in the measurement corresponding to the sleep state.

More specifically, the physiological sensors 270 optionally include sensors for detecting movement and minute ventilation in the patient. The physiological sensors 270 may include a position sensor and/or a minute ventilation (MV) sensor to sense minute ventilation, which is defined as the total volume of air that moves in and out of a patient's lungs in a minute. Signals generated by the position sensor and MV sensor are passed to the microcontroller 220 for analysis in determining whether to adjust the pacing rate, etc. The microcontroller 220 monitors the signals for indications of the patient's position and activity status, such as whether the patient is climbing upstairs or descending downstairs or whether the patient is sitting up after lying down.

The stimulation device additionally includes a battery 276 that provides operating power to all of the circuits shown in FIG. 2. For the stimulation device 100, which employs shocking therapy, the battery 276 is capable of operating at low current drains for long periods of time (e.g., preferably less than 10 mu A), and is capable of providing high-current pulses (for capacitor charging) when the patient requires a shock pulse (e.g., preferably, in excess of 2 A, at voltages above 2 V, for periods of 10 seconds or more). The battery 276 also desirably has a predictable discharge characteristic so that elective replacement time can be detected. Accordingly, the device 100 employs a lithium iodide and/or silver vanadium oxide batteries.

The stimulation device 100 can further include magnet detection circuitry (not shown), coupled to the microcontroller 220, to detect when a magnet is placed over the stimulation device 100 to perform various test functions of the stimulation device 100 and/or to receive or transmit data to the microcontroller 220 through the telemetry circuits 264.

The stimulation device 100 further includes an impedance measuring circuit 278 that is enabled by the microcontroller 220 via a control signal 280. The known uses for an impedance measuring circuit 278 include, but are not limited to, lead impedance surveillance during the acute and chronic phases for proper lead positioning or dislodgment; detecting operable electrodes and automatically switching to an operable pair if dislodgment occurs; measuring respiration or minute ventilation; measuring thoracic impedance for determining shock thresholds; detecting when the device has been implanted; measuring stroke volume; and detecting the opening of heart valves, etc. The impedance measuring circuit 278 is advantageously coupled to the switch 226 so that any desired electrode may be used.

In the case where the stimulation device 100 is intended to operate as an implantable cardioverter/defibrillator (ICD) device, it detects the occurrence of an arrhythmia, and automatically applies an appropriate therapy to the heart aimed at terminating the detected arrhythmia. To this end, the microcontroller 220 further controls a shocking circuit 282 by way of a control signal 284. The shocking circuit 282 generates shocking pulses of low (up to 0.5 J), moderate (0.5 J to 10 J), or high energy (11 J to 40 J), as controlled by the microcontroller 220. Such shocking pulses are applied to the patient's heart 102 through at least two shocking electrodes, and as shown in this embodiment, selected from the left atrial coil electrode 126, the RV coil electrode 132, and/or the SVC coil electrode 134. As noted above, the housing 200 may act as an active electrode in combination with the RV electrode 132, or as part of a split electrical vector using the SVC coil electrode 134 or the left atrial coil electrode 126 (i.e., using the RV electrode as a common electrode).

Cardioversion level shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5 J to 40 J), delivered asynchronously (since R-waves may be too disorganized), and pertaining exclusively to the treatment of fibrillation. Accordingly, the microcontroller 220 is capable of controlling the synchronous or asynchronous delivery of the shocking pulses.

In the following, there will be described an exemplifying embodiment for vagal stimulation of the right vagus nerve proximate to the azygos vein. First, with reference to FIGS. 3 and 4, a description of the relevant anatomy is provided.

Figure 3:
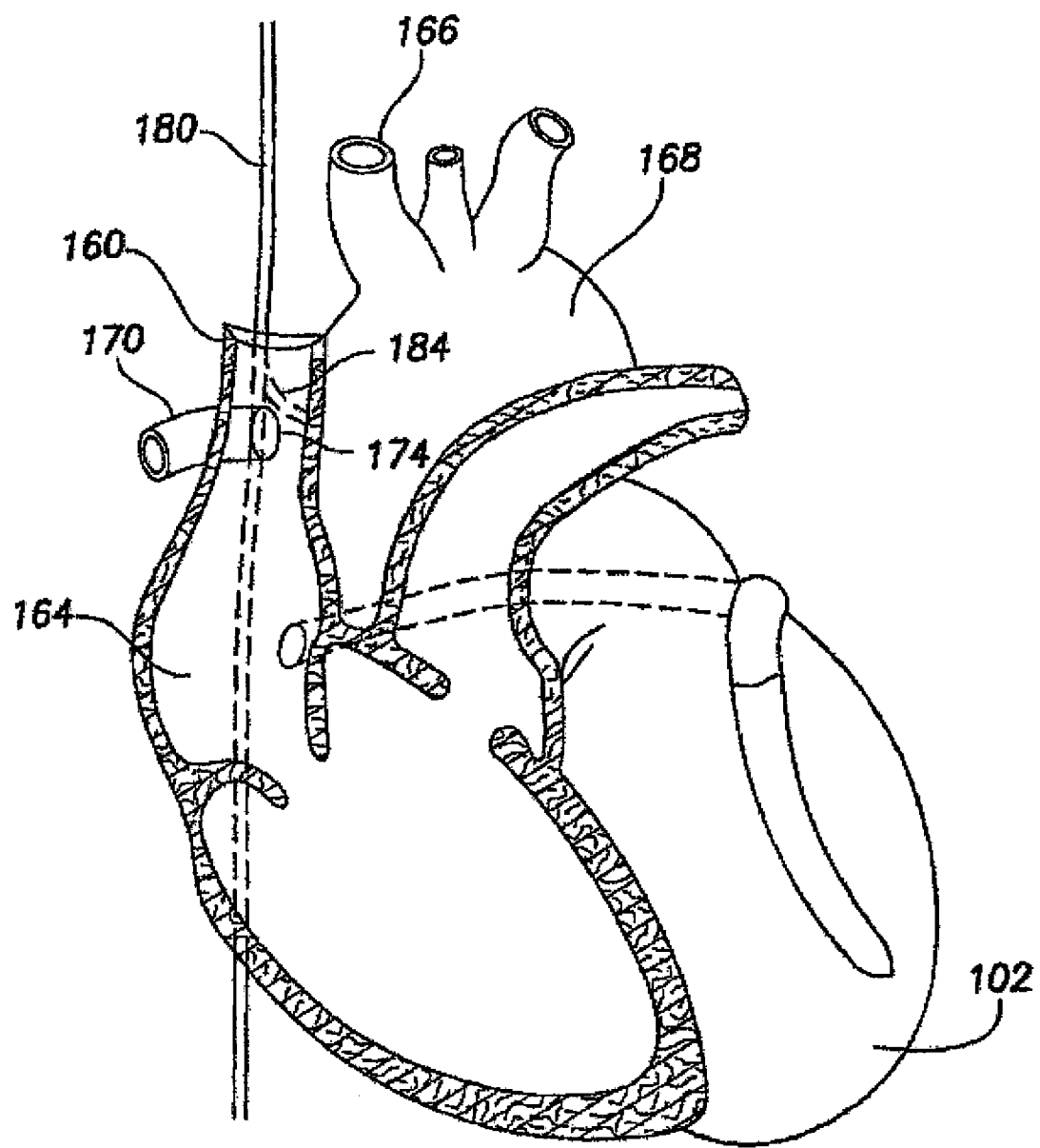
FIG. 3 is an approximate anatomical anterior cross-sectional view of a human heart that shows the azygos vein and the right vagus nerve.

Referring to FIG. 3, a heart 102 and a right vagus nerve 180 are shown. FIG. 3 also shows part of an azygos vein 170, particularly the portion that forms at least part of the "azygos arch" and connects with the heart's superior vena cava 160. The juncture or opening 174 between the azygos vein 170 and the superior vena cava 160 may be considered the end of the azygos vein, where deoxygenated blood enters the superior vena cava 160 en route to the heart's right atrium 164. The azygos vein 170 begins at the union of the right subcostal vein and the right ascending lumbar vein. The azygos vein 170 enters the thorax by passing through the aortic hiatus or by passing through or behind the right crus of the diaphragm. The azygos vein 170 passes upward through the posterior mediastinum near the midline just anterior to the bodies of the thoracic vertebrae or slightly to the right side of the vertebral bodies. At the level of the fourth thoracic vertebra the azygos vein 170 arches anteriorly over the root structures of the right lung to drain into the superior vena cava 160 usually just above the point where the superior vena cava 160 penetrates the pericardium. As the azygos vein 170 passes upward through the posterior mediastinum it lies just to the right of the thoracic duct which is just to the right of the descending aorta.

The hemiazygos vein (not shown) begins at the union of the left ascending lumbar vein and the left subcostal vein. It passes upward into the thorax through the left crus of the diaphragm or through the aortic hiatus. It receives the caudal three or four left posterior intercostal veins and crosses the midline at about the level of the ninth thoracic vertebra to drain into the azygos vein 170. As it crosses the midline it passes dorsal to the aorta, the esophagus and the thoracic duct.

FIG. 3 also shows a general depiction of the heart's aortic arch 168. The aortic arch 168 passes backwards and to the left behind the right half of the munubrium. Crossing the aortic arch 168 anterolaterally are the left phrenic, left vagus, left vagal cardiac branch and left sympathetic cardiac branch (not shown). As the left vagus reaches the inferior border of the aortic arch 168 it gives off the left recurrent laryngeal nerve, which passes backwards around the ligamentum arteriosum, to ascend between the trachea and esophagus. The upper part of the aortic arch 168 gives rise to the brachiocephalic trunk, left common carotid and left subclavian arteries.

Referring again to FIG. 3, the right vagus nerve 180 descends along the innominate artery 166 (also known as the brachiocephalic trunk) and passes medial to the arch of the azygos vein 170 to lie on the right of the trachea. The right vagus nerve 180 also gives rise to a cardiac nerve branch 184 supplying the heart 102. This branch 184 forms a plexus located between the aortic arch 168 and the bifurcation of the trachea. Thus, the right vagus cardiac nerve branch 184 (and/or plexus) passes proximate to the azygos vein 170, in particular, proximate to the arch of the azygos vein 170.

Figure 4:
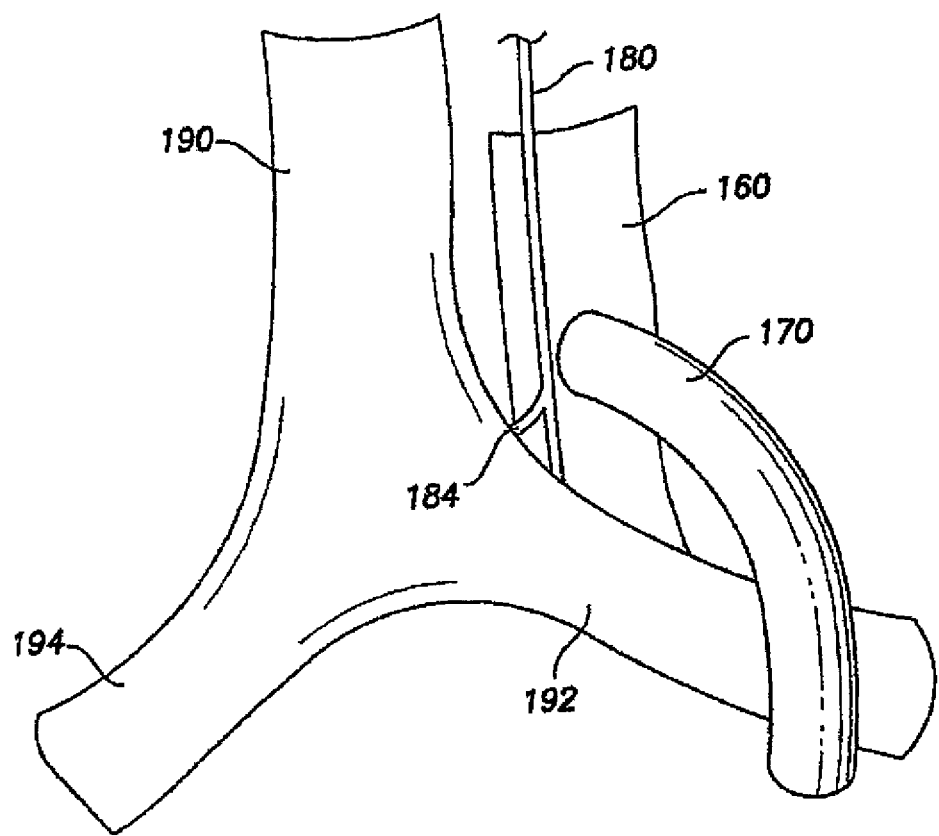
FIG. 4 is an approximate anatomical posterior view showing part of a human trachea, part of the azygos vein, part of the right vagus nerve and part of the superior vena cava.

A posterior illustration of the general anatomy of the aforementioned region appears in FIG. 4. As shown in FIG. 4, the arch of the azygos vein 170 arches over the right bronchus 192 near the bifurcation of the trachea 190. The trachea 190 bifurcates into a right bronchus 192 and a left bronchus 194. Not shown in FIG. 4 are the innominate artery 166 and the right branch of the pulmonary artery, which is medial to the right bronchus 192 and the superior vena cava 160 and anterior to the right vagus nerve 180.

While variation in anatomy typically occurs from one patient to another, the right innominate and the left innominate vein join together and meet the superior vena cava 160 at a vertical point approximately equal to the vertical point where the innominate artery 166 exits the aortic arch 168. From the superior vena cava 160, the left innominate vein passes anterior to the innominate artery 166, in a direction away from the right vagus nerve 180 and towards the left vagus nerve (not shown). As mentioned, the left vagus nerve crosses the aortic arch 168 anterolaterally whereas the right vagus nerve 180 passes posterior to the aortic arch 168 and hence, generally does not contact the surface of the left innominate vein.

For purposes of this discussion, it is the right vagus nerve that is of interest as it is believed to be controlling the Sinus Node and atrial rate, in general, whereas the left vagus nerve is believed to have a greater influence on the A-V Node.

Thus, an exemplary method presented herein includes positioning a lead having at least one electrode in a patient's azygos vein proximate to the right vagus nerve and preferably near the cardiac branch; and stimulating the patient's right vagus nerve and/or right vagal cardiac branch using the at least one electrode. Several exemplary leads are presented herein that include at least one electrode for positioning in a patient's azygos vein and stimulating the patient's right vagus nerve and/or right vagal cardiac branch.

In instances where an azygos vein portion of the lead includes a plurality of electrodes, positioning portions and/or features alleviate the need for selecting an electrode, or electrodes, amongst the plurality of electrodes to provide for adequate right vagus nerve stimulation.

Figure 5:
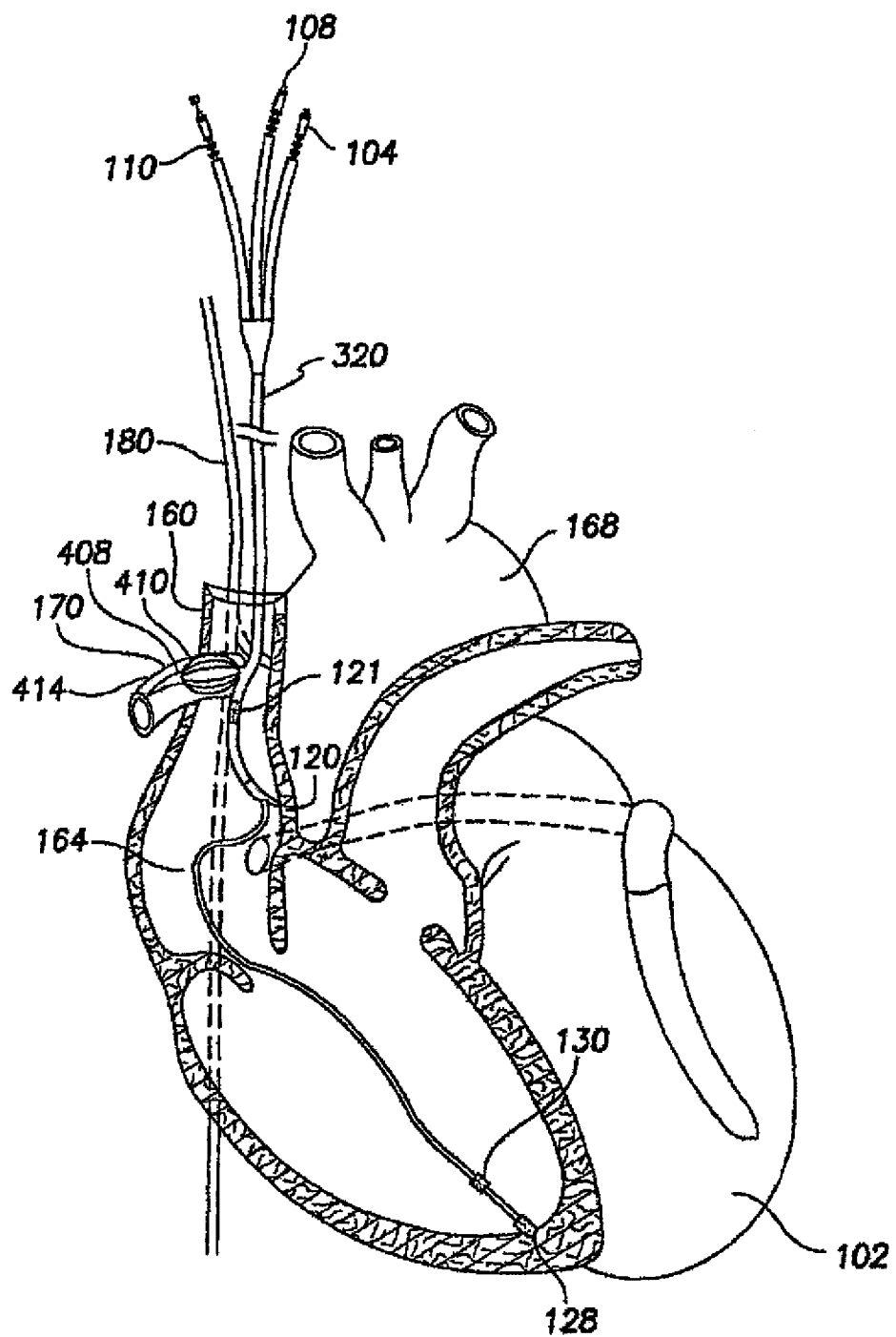
FIGS. 5 and 6 illustrate two leads, respectively, having electrodes for stimulating the vagal nerve through placement in or near the azygos vein in a location proximate to the vagal nerve and/or the cardiac branch.
Figure 6:
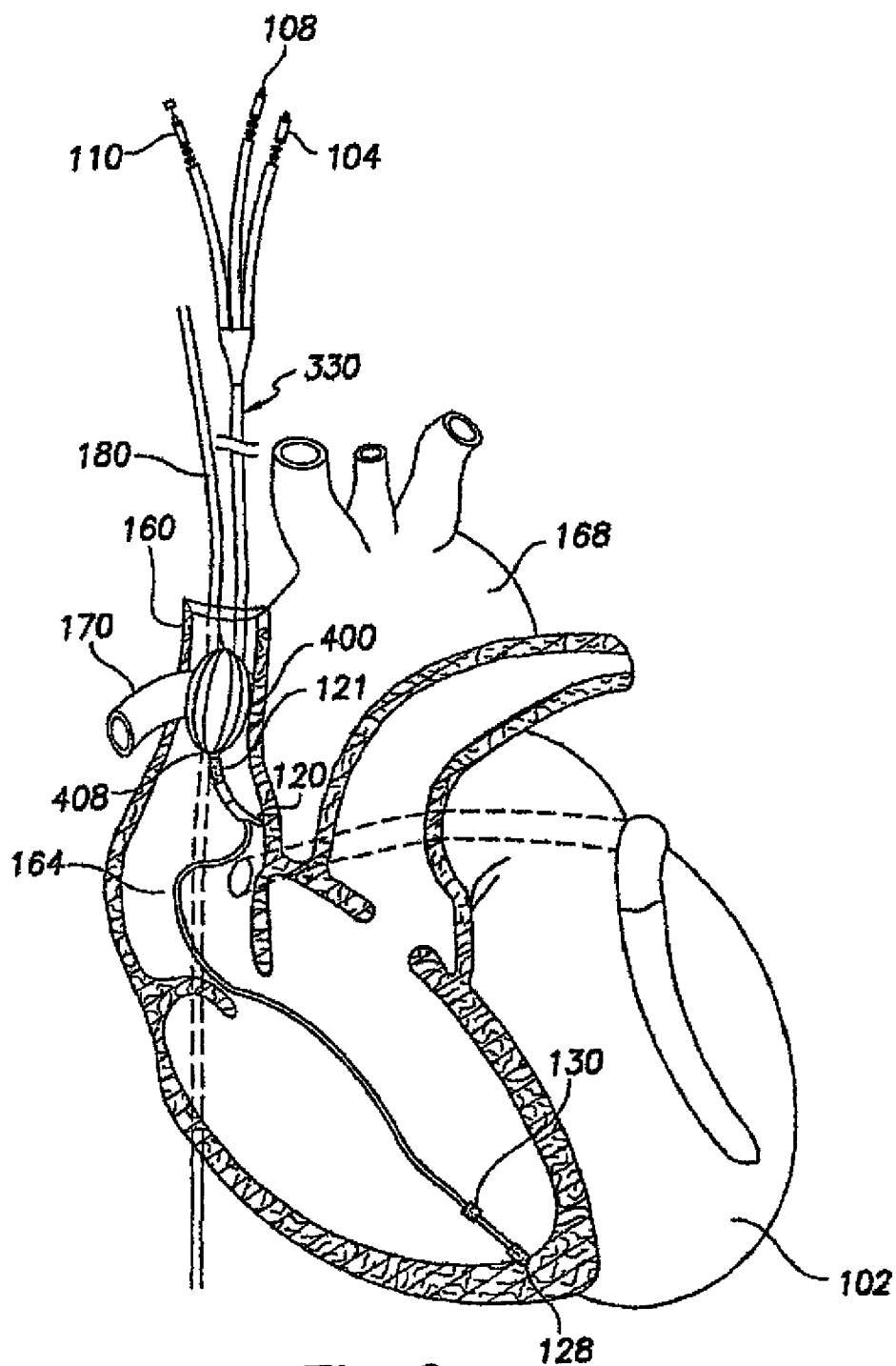

FIGS. 5 and 6 show two exemplary leads having at least one electrode capable of stimulating a patient's vagus nerve, respectively. Both of these leads share various features with the leads presented in FIG. 1 and are suitable for use with the device 100 described with reference to FIG. 2. In particular, the leads shown in FIGS. 5 and 6 include, in various combinations of connections similar to those presented in FIG. 1, e.g., such as, the right atrial connection 104, and/or the right ventricular connection 108. However, leads shown in FIGS. 5 and 6 further include a vagal connection 110, that is, a conductor and electrode(s) suitable for stimulating the vagus nerve. Further examples of leads can be found in EP 1 304 135 A2, which is incorporated herein by reference in its entirety.

FIG. 5 illustrates a single-pass A-V lead 320 that combines the functions of the right atrial connection 104 and the left ventricular connection 108, and further adds a vagal connection 110 (i.e., shown here for simplicity as a separate proximal connector coupled to a respective conductor). As shown in this embodiment, the vagal connection 110 is coupled to a deployable electrode (e.g., a basket electrode in this embodiment), and a distal end 408 with the stabilizing tail portion 414 (FIG. 7), and further includes atrial and ventricular pacing and sensing support using at least one ventricular electrode (128, 130, or both) and at least one atrial electrode (120, 121 or both). The advantages of the embodiment is that it supports A-V sensing, which is valuable for monitoring A-V dissociation (e.g., a partial or total interruption of the conduction from the atria to the ventricle, including prolongation of A-V conduction, first degree block (Mobitz I), second degree block (Mobitz II), or third degree A-V block) during vagal stimulation.

FIG. 6 illustrates a single-pass lead that combines the functions of the right atrial connection 104 and the left ventricular connection 108, with an "in-line" vagal connection 110. As shown in this embodiment, the vagal connection 110 is coupled to a deployable electrode (e.g., a basket electrode in this embodiment), and a distal end 408, which continues "in-line" to form at least one ventricular electrode (128, 130, or both) and at least one atrial electrode (120, 121 or both). In this embodiment, lead body between the atrial electrode 120 and the vagal electrode 400 (not shown to scale) may be configured to provide sufficient slack, or an atrial-J type shape, to allow placement of the atrial electrode 120 and further to allow the vagal electrode to be deployed against the SVC wall in a desired region near, or proximate, to the cardiac branch which will achieve a desired rate reduction by vagal stimulation.

While specific electrode combinations are shown, it is also within the scope of the application to add ring or coil electrodes in the atrium, or ventricle, or both and return electrodes in the SVC, as desired, to enhance tachyarrhythmia therapy.

While specific stabilization techniques have been shown, a lead may include any stabilization technique, such as, a hook, a tine, a spiral and/or a wiggle for securing the lead in a vessel by actively or passively fixating or otherwise biasing against the vessel to anchor the lead into position. For example, a preformed "S" wiggle (such as the one disclosed in U.S. Pat. No. 6,319,230, incorporated herein by reference) can secure a lead within a vessel by applying a force to bias against the vessel. The leads described herein optionally include at least one hook, tine, spiral, and/or wiggle.

Figure 7:
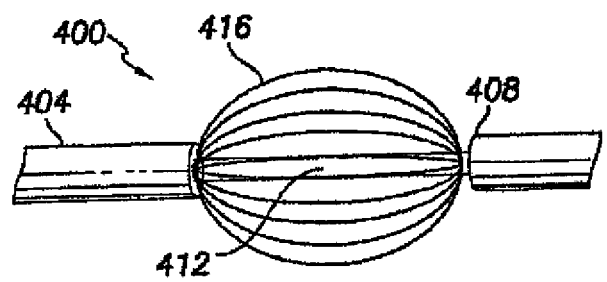
FIG. 7 illustrates an example of a vagus nerve stimulating electrode in the shape of a basket.

FIG. 7 shows an exemplary deployable or expandable electrode portion (400) suitable for use in the azygos vein. More specifically, the electrode portion (400) includes a proximal portion (404) and a distal portion (408). Substantially positioned between the proximal portion (404) and the distal portion (408) is at least one electrode (416). Optionally, a shaft (412) may exist between the proximal or distal end to provide structural support. Alternatively, the electrodes (416) may be pre-shaped to attain their expanded state without a shaft. Further examples of electrode portions are found in EP 1 304 135 A2, which was incorporated by reference above.

The electrode portion 400 shown in FIG. 7 includes an electrode "basket" 416 or "basket electrode", which optionally includes more than one electrode. The basket electrode may be a length of exposed conductor, or individually placed electrodes, or an array of electrodes, as shown and described in U.S. Pat. Nos. 5,782,239 and 5,411,025, which patents are hereby incorporated by reference in their entirety. In the embodiment using the "side-arm" configuration (e.g., FIG. 5) in which the vagal electrode is placed in the azygos vein rather than "in-line" near the SVC, an array of electrodes can be oriented or concentrated to face toward the tissue proximate to the cardiac branch. Upon implantation of such a lead, the side-arm and array of electrodes would self-orient towards the appropriate tissue.

Several methods, well known in the art, may be used to deploy the electrode portion. For example a stylet may be used to position the lead body into position and upon remove, the electrode will expand to its preformed shape. Alternately, a guiding sheath, or pull wire, may be used. For example, U.S. Pat. No. 5,411,025 discloses an outer catheter or sheath that holds the basket in its undeployed state during implant. U.S. Pat. No. 5,782,239 also discloses a puller wire which causes the basket to extend to its fully deployed state. These patents have already been incorporated herein by reference above. Balloon mechanisms/methods, expansion mechanisms/methods for expanding and/or securing leads are also known to one of ordinary skill in the art.

While only one configuration have been disclosed (i.e. a basket electrode), this is for illustration purposes only as other deployable electrode configurations dimensioned to fit the desired location (e.g., azygos vein or SVC near the cardiac branch) are also possible. Furthermore, details of alternative "self-orienting" electrodes, that is, electrode configurations that would concentrate the current density in a direction towards the tissue adjoining the vagal and cardiac branch nerves, can be found in the above referenced EP 1 304 135 A2.

There will now be described, with reference to FIGS. 8 and 9, exemplifying methods of a simulated heart rate turbulence (HRT) procedure, as well as a check for determining whether intrinsic HRT is present.

Figure 8:
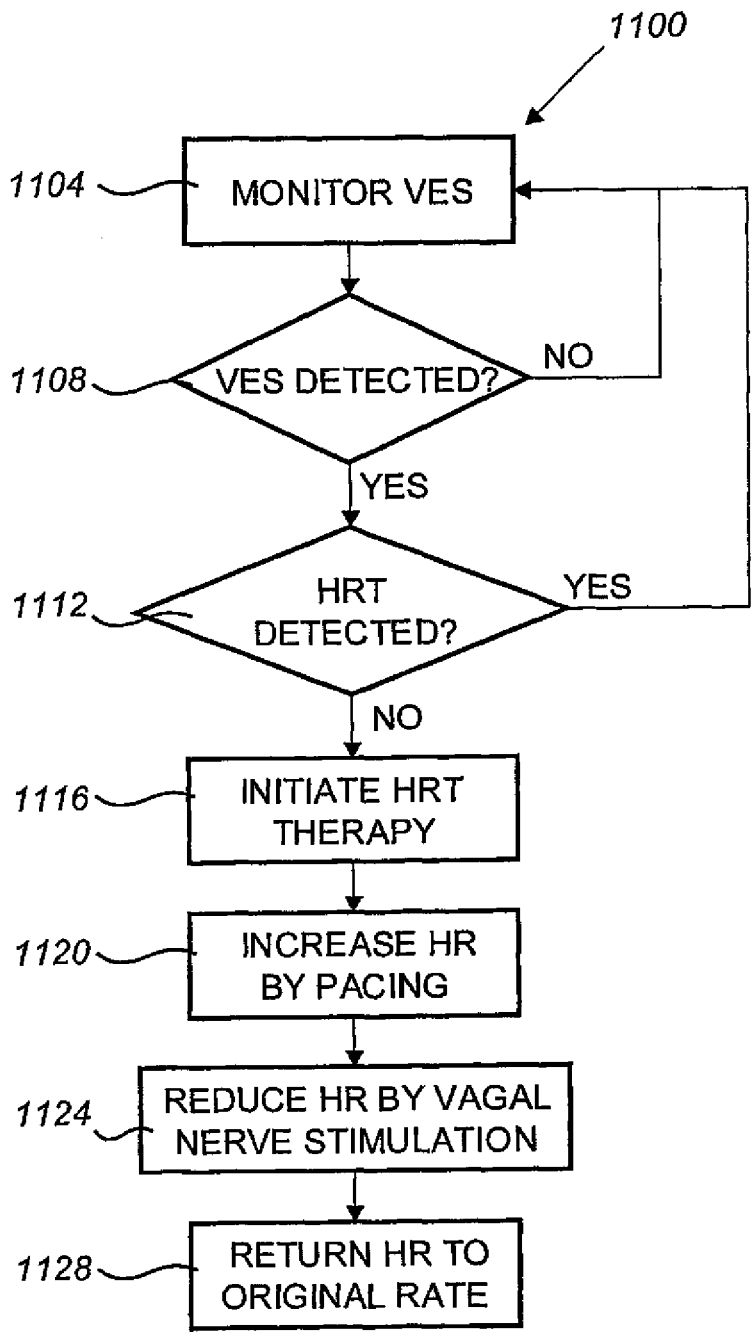
FIG. 8 is a functional block diagram of a method for applying a simulated heart rate turbulence procedure to a human heart in absence of an intrinsic heart rate turbulence response.

Turning first to FIG. 8, a step diagram of an exemplary method 1100 is presented. A monitoring step 1104 for detecting a premature cardiac contraction is provided. In this example, the system checks for ventricular extra systole (VES). However, the described example would be equally applicable to any other premature contraction, of any of the atria or ventricles. As long as no VES is detected, the monitoring is maintained.

If, at step 1108, a VES has been determined, then a determination of whether intrinsic HRT is present is performed at step 1112. This can be determined by measuring the RR interval between the two consecutive heart beats following the premature cardiac event and the ensuing compensatory pause, and compare said interval to, e.g. the existing RR interval prior to the premature cardiac event. Furthermore, more traditional HRT measurement may be combined with other criteria for determining the level or presence of intrinsic HRT, such as blood pressure, mechanical activation, sensor inputs, etc.

It should be noted that step 1112 may be omitted if it has been previously established that the patient lacks an adequate intrinsic HRT response, either through measurements prior to implantation, or determined by the system itself after implantation, e.g. using the method to be described below.

If it has been determined that there is no intrinsic HRT response, HRT therapy is initiated at step 1116. Optionally, a back-up pacing pulse may be provided immediately prior to initiating HRT therapy.

At step 1120, the first phase of HRT therapy is provided by delivering pacing pulses to cardiac tissue at an increased heart rate during, for example, about 2-4 beats. The heart rate is then gradually increased by, for example, about 2-4 percent for each beat.

Then, at step 1124, the second phase of the HRT therapy is provided by delivering vagal stimulation pulses to a vagus nerve site. Such vagal stimulation is delivered for about 7-10 heart beats and is intended to result in a gradual decrease in the heart rate of about 2 4 percent for each beat. Thereby, the heart rate will be slowed down to a level that is lower than the pre-existing heart rate, i.e. the heart rate present prior to the premature cardiac event that triggered the HRT therapy. Examples of a system and electrodes for vagal stimulation are given above, and a method of determining appropriate vagal stimulation parameters in order to obtain a desired heart rate reduction will follow.

Following the heart rate increase and ensuing decrease of the simulated HRT therapy procedure, there will be a gradual return, i.e. increase, of the heart rate to the level prior to the premature cardiac event. This may be achieved by providing pacing pulses with a gradually increasing rate. Alternatively, no pacing pulses are provided and the intrinsic rate of the heart will return to the desired level upon by simply ceasing the vagal stimulation. Of course, the two alternatives may be combined by monitoring the increase degree of the intrinsic heart rate and provide pacing pulses at an increased rate if required.

Even though specific ranges for duration of the different phases of the HRT therapy and the degree of gradual heart rate changes have been provided above in relation to the described exemplifying embodiment, this is merely for exemplary purposes. Other durations and levels of heart rate changes are of course contemplated without departing from the scope of the present application, preferably in adaptation to needs and requirements of the particular patient. For example, the HRT therapy could be slower and longer, i.e. with a smaller heart rate change from beat to beat but a longer duration for each phase, or quicker and shorter, i.e. with a larger heart rate change from beat to beat but a shorter duration for each phase. Also, the heart rate change could be provided with a greater degree of between a first pair of successive heart beats, and to a smaller degree or not at all between a second pair of successive heart beats within the same HRT therapy episode.

Furthermore, the number of beats during each phase could be programmable and/or optimized by the device for improving patient performance. Also, the amount of gradual rate increase and decrease, respectively, by each successive pulse in the different phases could be programmable values, and/or be optimized by the device for improving performance.

Figure 9:
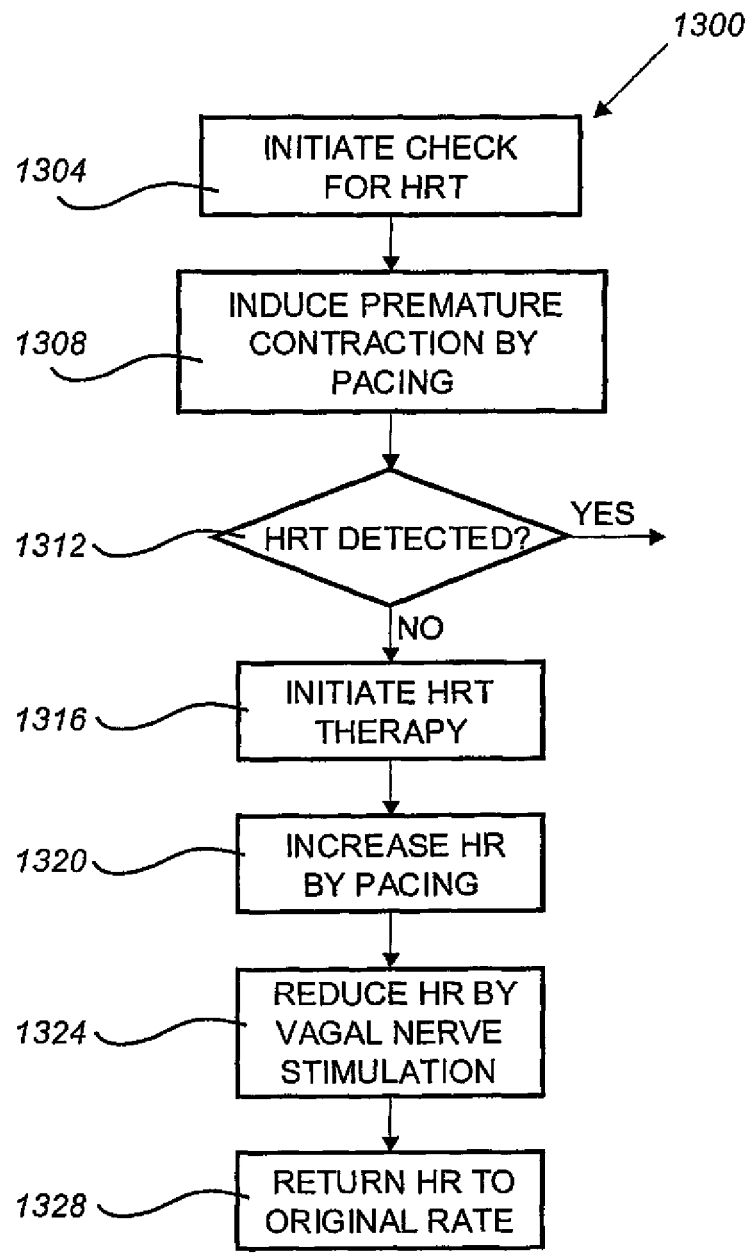
FIG. 9 is a functional block diagram of a method for determining the presence of an intrinsic heart rate turbulence response.

With reference now to FIG. 9, a simplified step diagram of an exemplary method 1300 for determining the presence and level of an intrinsic HRT response is presented.

According to the described example, a check for determining whether an intrinsic HRT response is present, and at a sufficient level, is initiated at step 1304.

At step 1308, a premature cardiac contraction is induced by the system through the delivery of a pacing pulse to a cardiac tissue site immediately following the end of the refractory period for the site. The site could be in the atrium or the ventricle of the heart. In a healthy heart, the resulting premature cardiac contraction, atrial or ventricular, would induce an intrinsic HRT response.

The response of the heart is then monitored, at step 1312, and an assessment of whether the intrinsic HRT response, if any, is performed. This is for instance performed by measuring the RR intervals for the heart beats immediately following the induced premature contraction. Thus, even though some sort of intrinsic HRT response can be detected, the response could still be determined to be inadequate. For example, the intrinsic HRT response could present an unsatisfactory heart rate increase, i.e. the heart rate does not increase to the same extent as in a healthy heart during HRT, the onset of HRT is delayed, the extent of heart rate decrease is reduced, etc.

Optionally, if it is determined that there is no intrinsic HRT response, an HRT therapy episode is immediately initiated at step 1316. Then, in the following steps 1320-1328, the system provides an HRT therapy in similar manner as described above in relation to method steps 1120 1128.

Furthermore, if an initial HRT response has been determined to be inadequate or altogether absent, the simulated HRT procedure may be activated such that an HRT therapy episode is initiated and performed following each premature cardiac event. Alternatively, said determination of the presence of an intrinsic HRT response may use the result from a number of pacer induced measurements. Then, the results of a number, e.g. 5, of premature events may be used for determining the degree of HRT of a patient's heart.

The leads presented herein and equivalents thereof are suitable for stimulating a patient's vagus nerve. There will now be described an exemplary method of varying intensities of applied vagal stimulation pulses at a vagus nerve site for obtaining a desired heart rate. In the exemplary method, in order to determine appropriate vagal stimulation parameters, the method applies vagal stimulation of varying intensities at a vagus nerve site until a desired reduced heart rate is achieved.

Advantageously, methods of vagal stimulation will have a slowing effect on rate of sinus node depolarization and possible AV nodal conduction velocity which will aid in the control of heart rhythms and/or to aid in remodeling of the heart. In particular, control of the vagal tone can enhance tachycardia therapy. In the present application, control of the vagal tone is utilized for inducing a simulated heart rate turbulence (HRT) procedure. Further methods of vagal stimulation can be found in the above referenced EP 1 304 135 A2, which methods are incorporated herein by reference.

According to the embodiments described herein, when determining appropriate vagal stimulation parameters, i.e.

parameters that will result in a desired heart rate decrease, the system will deliver vagal stimulation to the vagal nerve site(s). An exemplary method includes positioning an electrode portion of a lead in a patient's azygos vein and delivering an electrical signal to the electrode portion. In this exemplary method, the delivering optionally includes periodic delivery of an electrical signal having a desired magnitude. While fixed values may be programmed into the device based on implant testing, the system may for example automatically determine an appropriate level of vagal stimulation by determining a level of amplitude, pulse width and frequency that are most effective in attaining the desired heart rate. In a further embodiment, the system can also optimize the current drain by determining the most efficient combination of amplitude, pulse width and frequency that attains the desired heart rate.

Figure 10:
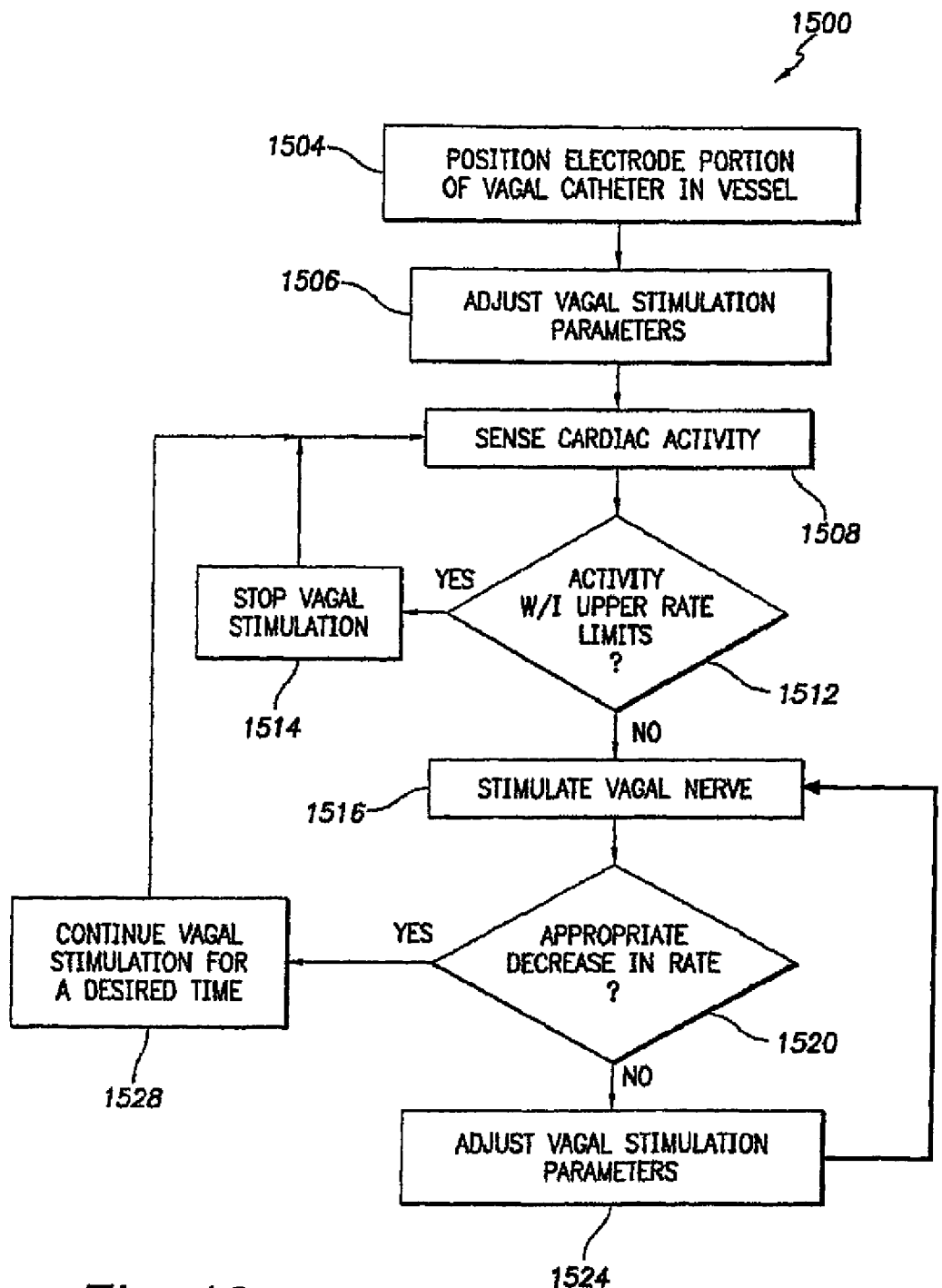
FIG. 10 is a functional block diagram of a method for stimulating a vagus nerve to slow heart rate when needed and automatically adjusting the stimulation intensity.

FIG. 10 shows a step diagram of an exemplary method 1500. A positioning step 1504 includes positioning of an electrode portion of a vagal lead in an appropriate vessel, such as, but not limited to, the azygos vein. An adjusting step 1506 adjusts vagal stimulation parameters (i.e., amplitude, pulse width and frequency). A sensing step 1508 senses cardiac activity, such as atrial heart rate. Next, a determination step 1512 determines whether the sensed cardiac activity is within desired limits. If yes at step 1512, then the set parameters will be stored and vagal stimulation will be disabled if it is currently turned on (at step 1514), and then returns to the sense step 1508 which continues to sense cardiac activity. Thus, the sensing of heart rate within a normal range is determined by the determination step 1512 periodically (or continuously).

If the sensed cardiac activity is not within the limits at step 1512, then a stimulation step 1516 causes stimulation of the vagus nerve. A determination step 1520 follows to determine if the vagal nerve stimulation causes an appropriate decrease in heart rate, e.g., a rate decrease by a selected degree of the previous rate or simply a rate decrease in the normal range. If a decrease in heart rate is detected in step 1520, then the method returns to the sensing step 1508.

If, on the other hand, an appropriate decrease in heart rate is not detected in step 1520, then an adjusting step 1524 further adjusts the vagal stimulation parameters and returns to the stimulation step 1516 and the determination step 1520. This process continues until a desired set of vagal stimulation parameters is found to achieve the desired heart rate, which parameters are then stored.

Once the desired heart rate is achieved (yes, at the determination step 1520), then vagal stimulation will continue for a desired time period (step 1528) (other pacing and/or monitoring functions being performed in the background as needed) until it is time to test to see if the underlying rhythm has returned to normal (steps 1508 and 1512) and, if so, then vagal stimulation can be turned off at step 1514. Thus, vagal stimulation is provided "on demand", that is, only when needed.

Figure 11:
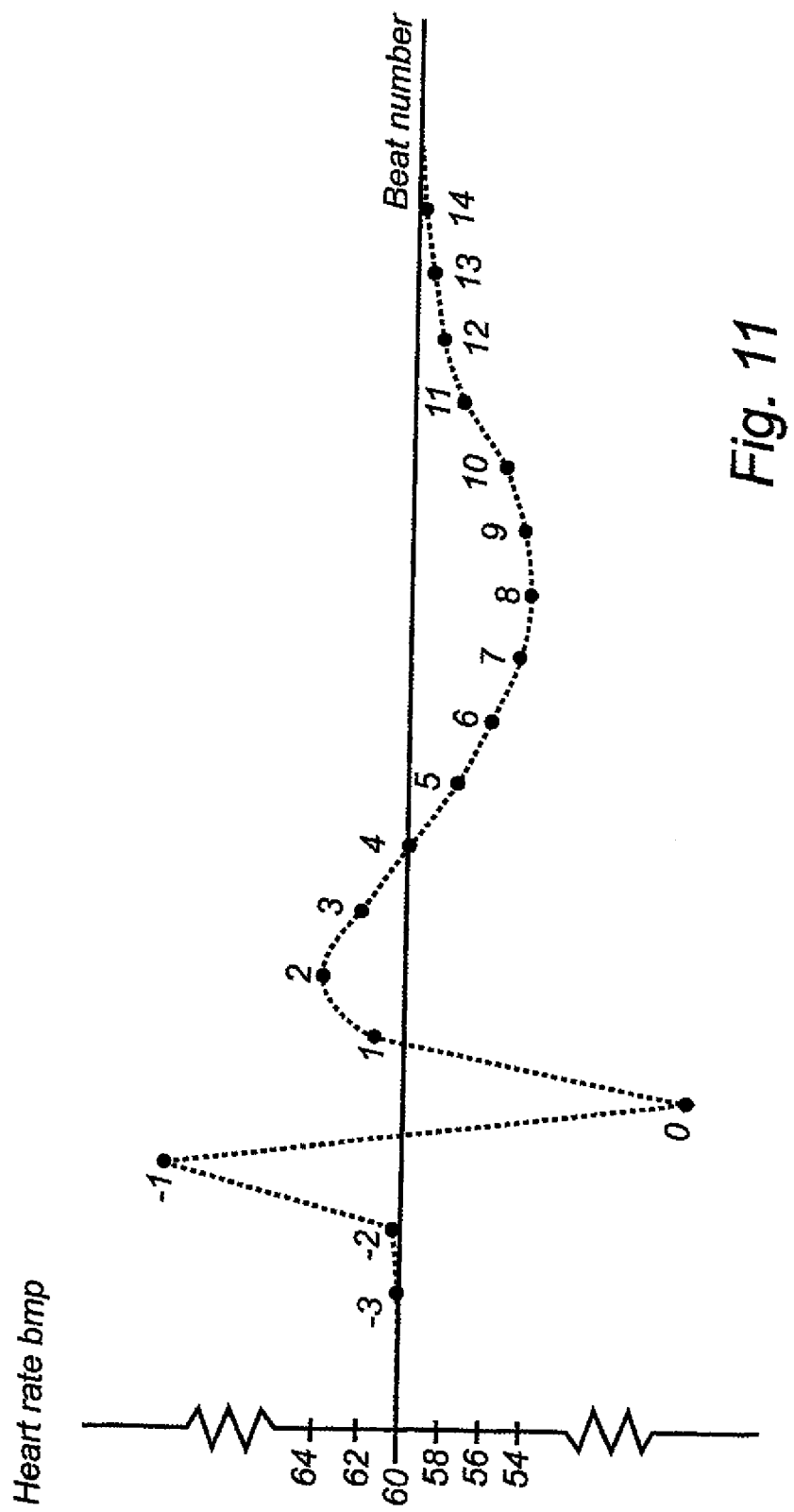
FIG. 11 is a diagram illustrating a premature cardiac event and an ensuing heart rate turbulence episode.

FIG. 11 is a diagram plot illustrating one example of variation in heart rate of a typical heart rate turbulence episode following a premature cardiac event. In the diagram, beats −3 and −2 are regular heart beats at a regular heart rate, i.e. the pre-existing heart rate, preceding a premature ventricular contraction, PVC. Beat −1 represents the PVC and beat 0 the first beat following the compensatory pause which generally follow upon a PVC. In FIG. 11, the heart rate for a particular beat is determined based on the time interval between the present beat and the preceding beat. This means that even though beat 0 is shown as having a reduced heart rate in relation to the pre-existing heart rate, beat 0 could nevertheless be regarded as the starting point for the heart rate turbulence episode. As seen in the figure, beats 1 and 2 occurs at an increased rate in relation to the pre-existing heart rate, reaching its maximum at beat number 2, and are followed by beats 3-8 at a gradually decreasing heart rate, reaching its minimum heart rate at beat number 8. Following the acceleration and deceleration phases of the HRT episode, beats 9-15 represent the gradual return of the heart rate to the pre-existing rate.

Even though FIG. 11 illustrates the intrinsic heart rate turbulence response to a PVC, the figure could also be used for illustrating a pacer induced heart rate turbulence episode. Then, stimulation pacing pulses may be delivered for providing said acceleration of heart rate, e.g. beats 0-2 of FIG. 11, vagal stimulation for providing the decrease of heart rate, e.g. beats 3-8 of FIG. 11, and pacing pulses again for brining the heart rate back to the pre-existing rate, e.g. beats 9-14 of FIG. 11. However, other alternatives are also contemplated. For instance, as mentioned above, pacing pulses could be delivered for providing all of the heart beats in an HRT episode, and/or pacing pulses could be inhibited by intrinsic cardiac activity. Furthermore, the return of the heart rate to, or close to, the pre-existing rate could be achieved by intrinsic cardiac activity while reducing vagal stimulation. Also, the diagram of FIG. 11 is merely an example of a HRT episode. As understood by the skilled person, the number of heart beats during each portion of the HRT episode, whether intrinsic or pacer induced, could of course vary, as well as the frequency of or time intervals between each beat.

Figure 12:
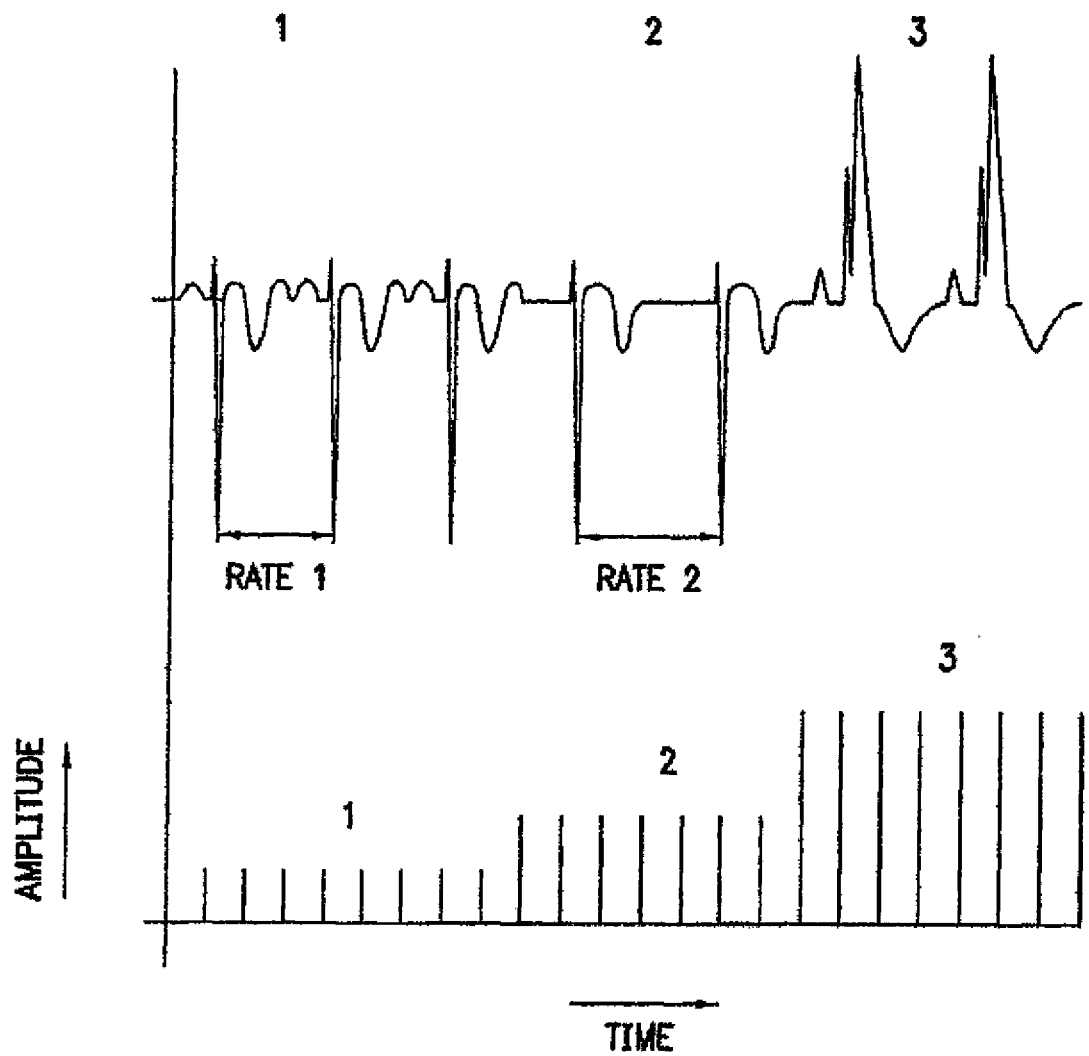
FIG. 12 is a plot of cardiac activity and pulse amplitude for vagal stimulation.

FIG. 12 illustrates several different responses to vagal stimulation. The upper plot shows cardiac activity with respect to time on a ECG strip while the lower plot shows vagal stimulation with respect to time. In both the upper and lower plots, three different segments, labeled I, II, and III, are shown. Rate I corresponds to vagal stimulation at a stimulation level that is insufficient to slow the rate. Rate II corresponds to a level of vagal stimulation that is sufficient to slow heart rate; thus, Rate II is less than Rate I. In the third segment, the level of vagal stimulation induces A-V dissociation which is observed on the ECG as being treated with backup ventricular pacing. For optimal results, vagal stimulation parameters should be adjustable to permit operation as shown in segment II.

As described with reference to FIG. 12, a given parameter combination that defines the intensity of the vagal stimulation may produce: (I) no decrease in heart rate; (II) a decrease in heart rate; or (III) A-V dissociation. If a decrease in heart rate has not occurred at step 1520, then further adjustment (e.g., increase) of a parameter or parameters is warranted, at the adjusting step 1524.

As described above, an exemplary implantable stimulation lead has an electrode portion capable of stimulation of the right vagus nerve with leads to the heart for stimulating parasympathetic nerves for decreasing atrial heart rate (and preferably, without stimulating the phrenic nerve which can evoke undesirable diaphragmatic stimulation). One particular location of stimulation includes the cardiac branch site where the right vagus nerve enters into the right atrium at the level of the SVC/RA junction, or just below the azygos vein.

Other exemplary methods, described herein, include adjusting vagal stimulation until a desired reduction in heart rate is achieved, while preserving sinus rhythm and A-V synchrony. In the event that provides backup A-V sequential support pacing is needed, the methods herein can be configured to do so in the event that asystole or A-V dissociation occurs.

Figure 13:
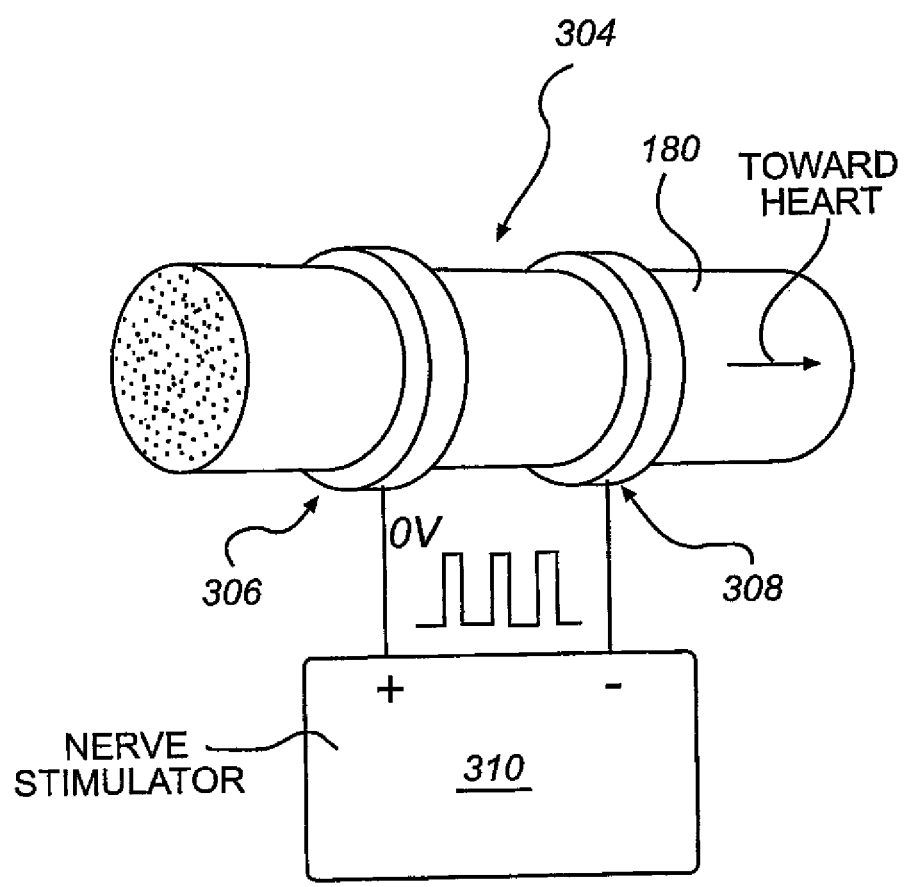
FIG. 13 illustrates a further example of a vagus nerve stimulating electrode in the form of a pair of annular sub-electrodes to be arranged around a vagus nerve.

FIG. 13 shows a further example of an electrode adapted for stimulation of a vagal nerve. In this example, an electrode (to be described below for the vagus nerve in conjunction with FIG. 13) in the system and electrode cable for a nerve to be stimulated can consist of one or more flexible electrical conductors made of, e.g., MP35, each conductor being enclosed in electrical insulation made of, e.g., silicone rubber. The collective silicone rubber insulation on the conductors serves as the electrode cable's outer sheath. The electrode is devised for bipolar stimulation and has a first sub-electrode for the cathode and a second sub-electrode for the anode.

The sub-electrodes can be devised as cuffs, rings, helices or the like with e.g. platinum, and other electrically conducting metals and/or polymers, as well as carbon fibers/meshes as electrode material in contact with the nerve and an electrically insulating and mechanically resilient sheath of silicone rubber around the electrode material. The silicone rubber is pretensioned to some degree so that electrode, after implantation, retains mechanical and electrical contact with the nerve. The electrode can also be provided with suturing appliances and a device for mechanically relieving the load on the sub-electrodes, e.g. silicone rubber anchoring around the nerve with tensile relief for the conductors of the sub-electrodes. The electrode may also be anchored, with a constructively adapted design, in a blood vessel, preferably a venous vessel, immediately adjacent to the nerve.

FIG. 13 shows the vagus nerve 180 and an electrode 304, consisting of a sub-electrode 306 arranged distal to the heart and a sub-electrode 308 arranged proximal to the heart, arranged thereon. The arrow in FIG. 13 points toward the heart. The sub-electrodes 306 and 308 are arranged for activating stimulation and are connected via conductors to the plus output terminal and the minus output terminal, respectively, of a nerve stimulator 310. If the sub electrode 306 lead to an anodic block, the result is that the main direction of nerve impulses is toward the heart.

Further details of this and other examples of electrodes for nerve stimulation can be found in U.S. Pat. No. 5,578,061, which is incorporated herein by reference in its entirety.

Although modifications and changes may be suggested by those skilled in the art, it is the intention of the inventors to embody within the patent warranted heron all changes and modifications as reasonably and properly come within the scope of their contribution to the art.

We claim as our invention:

1. An implantable heart stimulator comprising:
a cardiac pulse generator that generates and emits pacing pulses;
a cardiac lead connected to said cardiac pulse generator and configured to deliver said pacing pulses to cardiac tissue in at least one ventricle of a heart;
at least one cardiac lead carrying an electrode configured to detect electrical signals in the heart representative of cardiac contractions;
a vagal pulse generator that generates and emits vagal stimulation pulses;
at least one vagal lead configured to deliver said vagal stimulation pulses to a vagus nerve site;
a signal processing circuit configured to receive the electrical signals indicative of cardiac contractions and to process the received signals to determine therefrom whether a premature cardiac contraction has occurred, the signal processing circuit being further configured to determine whether heart rate turbulence is present in the received electrical signals in response to the detection of the occurrence of said premature cardiac contractions; and
a controller connected to said signal processing circuit to receive said output therefrom, said controller being configured to initiate a heart rate turbulence procedure to mimic heart rate turbulence by controlling said cardiac pulse generator to increase a rate of emission of said pacing pulses to initially accelerate the heart rate of said heart to an accelerated rate above an existing heart rate upon an occurrence of said premature contraction and the failure to detect heart rate turbulence, and to subsequently decelerate said heart rate to a decelerated rate below said existing heart rate by controlling said vagal stimulation pulse generator to produce a vagal response that decelerates the heart rate.

2. An implantable heart stimulator as claimed in claim 1 wherein said controller controls said pacing pulse stimulator to accelerate said heart rate for a period of time comprising 2 to 4 heartbeats.

3. An implantable heart stimulator as claimed in claim 2 wherein said controller is configured to adjust a duration during which said heart rate is accelerated dependent on patient response.

4. An implantable heart stimulator as claimed in claim 2 wherein said controller is configured to gradually accelerate said heart rate during said period.

5. An implantable heart stimulator as claimed in claim 4 wherein said controller is configured to gradually accelerate said heart rate with an increase of approximately 2% to 4% for each heartbeat.

6. An implantable heart stimulator as claimed in claim 4 wherein said controller is configured to adjust a degree of said gradual acceleration dependent on patient response.

7. An implantable heart stimulator as claimed in claim 1 wherein said controller is configured to control said vagal pulse stimulator to decelerate said heart rate during a period comprising 4 to 15 heartbeats.

8. An implantable heart stimulator as claimed in claim 7 wherein said controller is configured to adjust a duration of said period dependent on patient performance.

9. An implantable heart stimulator as claimed in claim 7 wherein said controller is configured to gradually decrease said heart rate during said period.

10. An implantable heart stimulator as claimed in claim 9 wherein said controller is configured to gradually decelerate said heart rate during said period by decreasing said heartbeat rate between 1% and 5% for each heartbeat.

11. An implantable heart stimulator as claimed in claim 10 wherein said controller is configured to adjust a degree of said gradual decrease of said heart rate dependent on patient response.

12. An implantable heart stimulator as claimed in claim 1 wherein said controller is configured to control said pacing pulse stimulator to increase the heart rate at an end of said heart rate turbulence procedure.

13. An implantable heart stimulator as claimed in claim 12 wherein said controller is configured to increase said heart rate to substantially equal said existing heart rate.

14. An implantable heart stimulator as claimed in claim 13 wherein said signal processing circuit monitors an intrinsic rate of the heart following said heart rate turbulence procedure, and wherein said controller is configured to control said pacing pulse stimulator to increase the heart rate to substantially equal said existing heart rate if said intrinsic rate does not increase to substantially equal said existing heart rate at said end of said heart rate turbulence procedure.

15. An implantable heart stimulator as claimed in claim 1 wherein said signal processing circuit is configured to detect a premature atrial contraction as said premature cardiac contraction.

16. An implantable heart stimulator as claimed in claim 1 wherein said signal processing circuit is configured to detect a premature ventricular contraction as said premature cardiac contraction.

17. An implantable heart stimulator as claimed in claim 1 wherein said signal processing circuit is configured to detect a contraction induced by an intrinsic cardiac event as said premature cardiac contraction.

18. An implantable heart stimulator as claimed in claim 1 wherein said signal processing circuit is configured to detect a contraction induced by delivery of stimulation pulses from said pacing pulse stimulator as said premature cardiac contraction.

19. A non-transitory computer-readable medium encoded with programming instructions for operating an implantable heart stimulator, said implantable heart stimulator comprising a cardiac pulse generator that generates and emits pacing pulses, a cardiac lead connected to said cardiac pulse generator and configured to deliver said pacing pulses to cardiac tissue in at least one ventricle of a heart, at least one cardiac lead carrying an electrode configured to detect electrical signals in the heart representative of cardiac contractions, a vagal pulse generator that generates and emits vagal stimulation pulses, at least one vagal lead configured to deliver said vagal stimulation pulses to a vagus nerve site, a signal processing circuit and a controller, said programming instructions causing:

said signal processing circuit to receive said electrical signals indicative of cardiac contractions and to determine therefrom whether a premature cardiac contraction has occurred, the signal processing circuit being further configured to determine whether heart rate turbulence is present in response to the detection of the premature cardiac contractions; and said controller to receive said output from said signal processing circuit and to initiate a heart rate turbulence procedure to mimic heart rate turbulence by controlling said cardiac pulse generator to increase a rate of emission of said pacing pulses to initially accelerate the heart rate of said heart to an accelerated rate above an existing heart rate upon an occurrence of said premature contraction and the failure to detect heart rate turbulence, and to subsequently decelerate said heart rate to a decelerated rate below said existing heart rate by controlling said vagal stimulation pulse generator to produce a vagal response that decelerates the heart rate.

20. A method for stimulating a heart, comprising the steps of;

receiving electrical signals indicative of cardiac contractions;

processing the electrical signals to determine whether a premature cardiac contraction has occurred, determining whether the patient is experiencing heart rate turbulence;

increasing a pacing rate to initially accelerate the heart rate of a patient's heart to an accelerated rate above an existing heart rate upon an occurrence of said premature contraction and a determination that the patient is not experiencing heart rate turbulence; and delivering vagal stimulation to produce a vagal response to decelerate the heart rate below the existing heart rate subsequent to the delivery of the pacing pulses at the increased pacing rate.

* * * * *